(12) United States Patent
Vlassenbroeck et al.

(10) Patent No.: US 9,050,280 B2
(45) Date of Patent: Jun. 9, 2015

(54) METHYLATION DETECTION OF MGMT

(75) Inventors: Ilse Vlassenbroeck, Sart-Tilman (BE); Katja Bierau, Wolfshausen (DE)

(73) Assignee: MDxHealth SA, Sart-Tilman (Liege) (BE)

( * ) Notice: Subject to any disclaimer, the term of this patent is extended or adjusted under 35 U.S.C. 154(b) by 580 days.

(21) Appl. No.: 12/678,706

(22) PCT Filed: Sep. 17, 2008

(86) PCT No.: PCT/GB2008/003145
§ 371 (c)(1),
(2), (4) Date: Jul. 9, 2010

(87) PCT Pub. No.: WO2009/037441
PCT Pub. Date: Mar. 26, 2009

(65) Prior Publication Data
US 2011/0287416 A1 Nov. 24, 2011

Related U.S. Application Data

(60) Provisional application No. 60/960,128, filed on Sep. 17, 2007.

(51) Int. Cl.
*C12Q 1/68* (2006.01)
*A61K 39/00* (2006.01)
*A61K 38/08* (2006.01)
*A61K 38/10* (2006.01)

(52) U.S. Cl.
CPC ............ *A61K 39/0011* (2013.01); *A61K 38/08* (2013.01); *A61K 38/10* (2013.01); *C12Q 1/6844* (2013.01); *C12Q 1/6886* (2013.01)

(58) Field of Classification Search
None
See application file for complete search history.

(56) References Cited

U.S. PATENT DOCUMENTS

| | | | |
|---|---|---|---|
| 4,437,975 A | 3/1984 | Gillespie et al. | |
| 6,090,552 A | 7/2000 | Nazarenko et al. | |
| 6,117,635 A * | 9/2000 | Nazarenko et al. | 435/6.11 |
| 6,331,393 B1 * | 12/2001 | Laird et al. | 435/6.12 |
| 6,410,276 B1 | 6/2002 | Burg et al. | |
| 6,426,217 B1 | 7/2002 | Chaux et al. | |
| 6,768,000 B1 | 7/2004 | Nardone | |
| 8,062,849 B2 * | 11/2011 | Sukumar et al. | 435/6.12 |
| 2004/0241824 A1 | 12/2004 | Schrenzel et al. | |
| 2006/0115835 A1 * | 6/2006 | Tetzner et al. | 435/6 |
| 2006/0129331 A1 * | 6/2006 | Akilesh et al. | 702/20 |
| 2006/0194208 A1 * | 8/2006 | Tetzner et al. | 435/6 |
| 2007/0059753 A1 * | 3/2007 | Vener et al. | 435/6 |
| 2008/0096768 A1 * | 4/2008 | Laird et al. | 506/9 |

FOREIGN PATENT DOCUMENTS

| | | |
|---|---|---|
| EP | 1491639 | 12/2004 |
| EP | 0912597 | 9/2005 |
| WO | 9006995 | 6/1990 |
| WO | 9118926 | 12/1991 |
| WO | 9400153 | 1/1994 |
| WO | 9517210 | 6/1995 |
| WO | 9602555 | 2/1996 |
| WO | 9633739 | 10/1996 |
| WO | 9850399 | 11/1998 |
| WO | 9940188 | 8/1999 |
| WO | 0009159 | 2/2000 |
| WO | 0062800 | 10/2000 |
| WO | 0134617 | 5/2001 |
| WO | 03046142 | 6/2003 |
| WO | 03065806 | 8/2003 |
| WO | 0021551 | 4/2004 |
| WO | 2004067726 | 8/2004 |
| WO | 2004087957 | 10/2004 |
| WO | 2005042713 | 5/2005 |
| WO | 2007147876 | 12/2007 |
| WO | 2008084219 | 7/2008 |

OTHER PUBLICATIONS

Esteller et al. (Inactivation of the DNA Repair Gene O6-Methylguanine-DNA Methyltransferase by Promoter Hypermethylation is a Common Event in Primary Human Neoplasia, Cancer Research, 59;793-, 1999).*
Agrelo et al., Epigenetic inactivation of the premature aging Werner syndrome gene in human cancer, PNAS, 103(23);8822-27, 2006).*
Khan et al., Pten Promoter Is Methylated in a Proportion of Invasive Breast Cancers, Int. J. Cancer, 112, 407-410, 2004.*
Kovacevic et al., The metastasis suppressor, Ndrg-1: A new ally in the fight against cancer, Carcinogenesis, 27(12);2355-66, Aug. 18, 2006.*
Rychlik et al., Optimization of the annealing temperature for DNA amplification in vitro, Nucleic Acids Res 18 (21): 6409-12, 1990.*
Real Time PCR CT Values (attached, May 2007).*
Maxwell et al. (Quantitative analysis of O6-alkylguanine-DNA alkyltransferase in malignant glioma, Mol Cancer Ther 2006;5(10). Oct. 2006).*

(Continued)

*Primary Examiner* — Christopher M Babic
*Assistant Examiner* — Aaron Priest
(74) *Attorney, Agent, or Firm* — Andrus Intellectual Property Law, LLP

(57) ABSTRACT

A real-time method of detecting the presence and/or amount of a methylated or unmethylated gene of interest in a DNA-containing sample, comprises the steps of: (a) contacting the DNA-containing sample with a reagent which selectively modifies unmethylated cytosine residues in the DNA to produce detectable modified residues but which does not modify methylated cytosine residues (b) amplifying at least a portion of the methylated or unmethylated gene of interest using at least one primer pair, at least one primer of which is designed to bind only to the sequence of methylated or unmethylated DNA following treatment with the reagent, wherein at least one primer in the primer pair produces a detectable fluorescence signal during amplification which is detected in real-time (c) quantifying the results of the real-time detection against a standard curve for the methylated or unmethylated gene of interest to produce an output of gene copy number.

22 Claims, 5 Drawing Sheets

(56) References Cited

OTHER PUBLICATIONS

House et al. (Molecular progression of promoter methylation in intraductal papillary mucinous neoplasms (IPMN) of the pancreas, Carcinogenesis vol. 24 No. 2 pp. 193-198, 2003).*

Calfice et al., "A new method for testing MGMT gene promoter methylation status of glioblastoma tissue using a direct, real-time fluorescence-based methylation-specific PCR", Jun. 2007, 77-78.

Esteller et al., "Hypermethylation of the DNA repair gene 0(6)-methylguanine DNA methyltransferase and survival of patients with diffuse large B-cell lymphoma", Journal of the National Cancer Institute, Jan. 2, 2002, 94(1):26-32.

House et al., "Molecular progression of promoter methylation in intraductal papillary mucinous neoplasms (IPMN) of the pancreas", Carcinogenesis, Feb. 2003, 24(2):193-198.

Maxwell et al., "Quantitative analysis of 06-alkylguanine-DNA alkyltransferase in malignant glioma", Molecular Cancer Therapeutics, Oct. 2006, 5(10):2531-2539.

Rickert et al., "Refinement of single-nucleotide polymorphism genotyping methods on human genomic DNA: amplifluor allele-specific polymerase chain reaction versus ligation detection reaction-TaqMan", Analytical Biochemistry, 2006, 330(2):288-297.

Tetzner, Entwicklung von Realtime-PCR-Methoden. zur Analyse von DNA-Methylierung, 2006, 1-122.

Tetzner, "Real-time PCR methods for methylation analysis", 2006, (English Translation), 1.3.1-1.3.4.

Vlassenbroeck et al., "Validation of real-time methylation-specific PCR to determine 0 <6>-methylguanine-DNA methyltransferase gene promoter methylation in flioma", Journal of Molecular Diagnostics, Jan. 1, 2008, 10 (4):332-337.

International Search Report for PCT/GB2008/003145 dated Jan. 20, 2009.

Written Opinion for PCT/GB2008/003145 dated Jan. 20, 2009.

Brandes et al., "Correlations Between O6-Methylguanine DNA Methyltransferase Promoter Methylation Status, 1p and 19q Deletions, and Resposne to Temozolomide in Anaplastic and Recurrent Oligodendroglioma: A Prospective GICNO Study", Journal of Clinical Oncology, Oct. 10, 200, 24(29): 4746.

Eads et al., "MethyLight: a high-throughput assay to measure DNA methylation", Nucleic Acids Research, 2000, 28 (8):e32.

Esteller et al., "Inactivation of the DNA Repair Gene O6-Methylguanine-DNA Methyltransferase by Promoter Hypermethylation is a Common Event in Primary Human Neoplasia", Cancer Research, 1999, 59:793-797.

Esteller et al., "Inactivation of the DNA-Repair Gene MGMT and the Clinical Response of Gliomas to Alkylating Agents", Journal of Medicine, Nov. 9, 2000, 343(19): 1350.

Esteller et al., "A gene hypermethylation profile of human cancer", Cancer Research, 2001, 61:3225-3229.

Frommer et al., "A genomic sequencing proocol that yields a positive display of 5-methylcytosine residues in individual DNA strands", Proc Natl Acad Sci, Genetics, Mar. 1992, 89: 1827-1831.

Hegi et al., "Clinical Trial Substantiates the Predictive Value of O-6-Methylguanine-Dna Methyltransferase Promoter Methylation in Glioblastoma Patients Treated with Temozolomide", Clinical Cancer Research, 2004, 10:1871-1874.

Hegi et al., "MGMT Gene Silencing and Benefit from Ttemozolomide in Glioblastoma", The New England Journal of Medicine, Mar. 10, 2005, 352(10):997.

Lacayo et al., "CpG Island Methylator Phenotype and Childhood Leukemia", Clin Cancer Res, 2006, 12:4787-4789.

Mikeska et al., "Optimization of Quantitative Mgmt Promoter Methylation Analysis Using Pyrosequencing and Combined Bisulfite Restriction Analysis", Journal of Molecular Diagnostics, Jul. 2007, 9(3): 368.

Mirmohammadsadegh et al., "Epigenetic Silencing of the PTEN Gene in Melanoma", Cancer Research, 2006, 66:6546-6552.

Ogino et al., "Precision and performance characteristics of bisulfite conversion and real-time PCT (MethyLight) for quantitative DNA methylation analysis", Journal of Molecular Diagnostics, May 2006, 8(2): 209.

Palmisano et al., "Predicting lung cancer by detecting aberrant promoter methylation in sputum", Cancer Research, 2000, 60: 5954-5958.

Perry et al., "The emerging roles of DNA methylation in the clinical management of prostate cancer", Endocrine-Related Cancer, 2006, 13:357-377.

Qian et al., Methylation Hot Spots in the 5' Flanking Region Denote Silencing of the O6-Methylguanine-DNA Methyltransferase Gene, Cancer Research, 1997, 57: 3672-3677.

Radonic et al., "Guideline to reference gene selection for quantitative real-time PCR", Biochemical and Biophysical Research Communication, 2004, 313:856-862.

Stojic et al., "High Doses of Sn1 Type Methylating Agents Activate DNA Damage Signaling Cascades that are Largely Independent of Mismatch Repair", Cell Cycle, Mar. 2005, 4(3):473-477.

Stupp et al., "Radiotherapy plus concomitant and adjuvant temozolomide for glioblastoma", The New England Journal of Medicine, Mar. 10, 2005, 352(10):987.

Stupp et al., "Changing Paradigms—An update on the multidisciplinary management of malignant glioma", The Oncologist, 2006, 11:165-180.

Watts et al., "Methylation of Discrete Regions of the O6-Methylguanine DNA Methyltransferase (MGMT) CpG Island is Associated with Heterochromatinization of the MGMT Transcription Start Site and Silencing of the Gene", Molecular and Cellular Biology, Sep. 1997, 17(9):5612-5619.

Yang et al., "Differential DNA methylation profiles in gynecological cancers and correlation with clinico-pathological data", BMC Cancer, 2006, 6:212.

Chomez et al., "An Overview of the MAGE Gene Family with the Identification of All Human Members of the Family", Cancer Research, Jul. 15, 2001, 61:5544-5551.

Criniere et al., "MGMT prognostic impact on glioblastoma is dependent on therapeutic modalities", J Neurooncol 2007, 83:173-9.

Everhard et al. "MGMT methylation: a marker of response to temozolomide in low-grade gliomas", Ann Neurol 2006, 60:740-3.

Fraley et al., "Model-Based Clustering, Discriminant Analysis, and Density Estimation", J American Statistical Assoc., 2002, 97:611-31.

Fraley et al., "MCLUST Version 3 for R: Normal Mixture Modeling and Model-based Clustering", vol. Washington: Department of Statistics, University of Washington, 2006.

Furuta et al., "Promoter methylation profiling of 30 genes in human malignant melanoma", Cancer Science, Dec. 2004, 95(12):962-968.

Gerson, "MGMT: its role in cancer aetiology and cancer therapeutics", Nat Rev Cancer 2004, 4:296-307.

Hoffman et al., "Causes and consequences of DNA hypomethylation in human cancer", Biochemistry and Cell Biology, 2005, 83:296-321.

Honda et al., "Demethylation of MAGE promoters during gastric cancer progression", British Journal of Cancer, 2004, 90:838-843.

Jang et al., "Activation of melanoma antigen tumor antigens occurs early in lung carcinogenesis", Cancer Research, Nov. 1, 2001, 61(21):7959-7963.

Kim et al., "Promoter hypomethylation and reactivation of MAGE-A1 and MAGE-A3 genes in colorectal cancer cell lines and cancer tissues", World Journal of Gastroenterology, Sep. 2006, 12(35):5651-5657.

Kong et al., "Real-time PCR detection of telomerase activity using specific molecular beacon probes", Anal Bioanal Chem, 2007, 388:699-709.

Laird, "The power and the promise of DNA methylation markers", Nat Rev Cancer 2003, 3:253-66.

Lucas et al., "Identification of a New MAGE Gene with Tumor-specific Expression by Representational Difference Analysis", Cancer Research, Feb. 15, 1998, 58:743-752.

Lucas et al., "A New MAGE Gene with Ubiquitous Expression Does Not Code for Known MAGE Antigens Recognized by T Cells", Cancer Research, Aug. 15, 1999, 59:4100-4103.

Lucas et al., "MAGE-B5, MAGE-B6, MAGE-C2, and MAGE-C3: Four new members of the MAGE family with tumor-specific expression", International Journal of Cancer, 2000, 87:55-60.

(56) References Cited

OTHER PUBLICATIONS

Muscatelli et al., "Isolation and characterization of a MAGE gene family in the Xp21.3 region", Proceedings of the National Academy of Science, May 1995, 92:4987-4991.

Pegg, "Repair of O(6)-alkylguanine by alkyltransferases", Mutat Res 2000, 462:83-100.

Qui et al., "5' CpG island methylation analysis identifies the MAGE-A1 and MAGE-A3 genes as potential markers of HCC", Clinical Biochemistry, Mar. 1, 2006, 39(3):259-266.

Takahashi et al., "Identification of MAGE-1 and MAGE-4 Proteins in Spermatogonia and Primary Spermatocytes of Testis", Cancer Research, Aug. 15, 1995, 55:3478-3482.

Vansteenkiste et al., Abstract of "Final results of a multi-center, double-blind, randomized, placebo-controlled phase II study to assess the efficacy of MAGE-A3 immunotherapeutic as adjuvant therapy in stage IB/II non-small cell lung cancer (NSCLC)", Journal of Clinical Oncology, Jun. 20, 2007 Supplement of ASCO Annual Meeting Proceedings, 25(18S):7554.

Zammatteo et al., "DNA Microarray to Monitor the Expression of MAGE-A Genes", Clinical Chemistry, 2002, 48 (1):25-34.

Zitt et al., "DNA methylation in colorectal cancer—Impact on screening and therapy monitoring modalities?" Disease Markers 2007, 23:51-71.

NEB catalog, 1996/1997, p. 111.

Exam Report for EP08806301.1 dated Sep. 13, 2010.

International Search Report for PCT/GB2008/003142 dated Jan. 22, 2009.

Written Opinion for PCT/GB2008/003142 dated Jan. 22, 2009.

* cited by examiner

METHYLATION DETECTION OF MGMT

CROSS-REFERENCE TO RELATED APPLICATIONS

This application is the U.S. national stage application of International Application PCT/GB2008/003145, filed Sep. 17, 2008, which international application was published on Mar. 26, 2009, as International Publication WO2009/037441 in the English language. The International Application claims priority of U.S. Provisional Patent Application No. 60/960,128 filed Sep. 17, 2007.

FIELD OF THE INVENTION

The present invention is concerned with detection of epigenetic modifications in nucleic acids. More specifically, the invention relates to methods of detecting methylated or unmethylated forms of a gene of interest. The methods of the invention involve amplification techniques, in particular fluorescence based real-time and end-point PCR methods.

BACKGROUND TO THE INVENTION

Gene methylation is an important regulator of gene expression. In particular, methylation at cytosine residues found in CpG di-nucleotide pairs in the promoter region of specific genes can contribute to many disease conditions through down regulation of gene expression. For example, aberrant methylation of tumour suppressor genes can lead to down regulation of these genes and is thus associated with the presence and development of many cancers. Patterns of aberrant gene methylation are often specific to the tissue of origin. Accordingly, detection of the methylation status of specific genes is of prognostic and diagnostic utility and can be used to both determine the relative stage of a disease and also to predict response to certain types of therapy.

O6-methylguanine-DNA methyltransferase (MGMT) is a cellular DNA repair protein that rapidly reverses alkylation (e.g. methylation) at the O6 position of guanine, thereby neutralizing the cytotoxic effects of alkylating agents used in therapy such as temozolomide (TMZ) and carmustine (1-3). It has been shown that epigenetic silencing of the MGMT gene by promoter silencing shuts down gene transcription (4, 5), and reflects a common alteration in primary human tumors that leads to MGMT deficiency (6). Epigenetic silencing of the MGMT gene has been shown to correlate with improved survival in several studies with glioma patients treated with alkylating agent therapy (7) and has been substantiated in two clinical trials (8, 9). The recent randomized clinical trial suggests that the MGMT-methylation status has a predictive value for benefit from the addition of the alkylating agent TMZ (9, 10). This finding has important clinical implications for stratified therapy (11). While this trial has established the new standard of care for glioblastoma patients (10), the benefit of the addition of TMZ chemotherapy was heavily weighted to patients whose tumors had a methylated MGMT promoter, with 46% still alive at 2 years, compared to only 14% of the patients with unmethylated MGMT (9). Hence, this epigenetic alteration in tumors can now be exploited in a diagnostic test to predict benefit from alkylating agent therapy for individualized management of patients. Beside glioblastoma, there is a published report that the MGMT methylation status may also predict benefit from alkylating agent containing therapy in patients with low grade glioma, oligodendroglioma, and diffuse large B-cell lymphoma (12, 13, 25)

Methylation-Specific PCR (MSP) with visualization of the results on a gel (gel-based MSP assay) is widely used to determine epigenetic silencing of genes (14), and in particular for testing MGMT promoter methylation in glioma (13, 15), although quantitative tests using other technologies have been developed (16-18). The nested gel-based MSP assay for MGMT has been used to establish the predictive value of the methylation status of the MGMT gene promoter in the clinical trials detailed above (8, 9). This methodology is highly sensitive and accurate, but has drawbacks for routine clinical use.

A number of fluorescence based technologies are available for real-time monitoring of nucleic acid amplification reactions. One such technology is described in U.S. Pat. No. 6,090,552 and EP 0912597 and is commercially known as Amplifluor®. This method is also suitable for end-point monitoring of nucleic acid amplification reactions.

SUMMARY OF THE INVENTION

The present invention relates to an improved method of detecting the presence/amount of a methylated or unmethylated gene of interest in a DNA-containing sample. The methods rely upon optimisation of a specific detection technique for real time or end point detection of amplification products in the context of methylation detection.

Accordingly, in a first aspect, the invention provides a real-time method of detecting the presence and/or amount of a methylated or unmethylated gene of interest in a DNA-containing sample, comprising:

(a) contacting/treating the DNA-containing sample with a reagent which selectively modifies unmethylated cytosine residues in the DNA to produce detectable modified residues but which does not modify methylated cytosine residues (b) amplifying at least a portion of the methylated or unmethylated gene of interest using at least one primer pair, at least one primer of which is designed to bind only to the sequence of methylated or unmethylated DNA respectively following treatment with the reagent, wherein at least one primer in the primer pair is a primer containing a stem loop structure carrying a donor and an acceptor moiety of a molecular energy transfer pair arranged such that in the absence of amplification, the acceptor moiety quenches fluorescence emitted by the donor moiety (upon excitation) and during amplification, the stem loop structure is disrupted so as to separate the donor and acceptor moieties sufficiently to produce a detectable fluorescence signal which is detected in real-time to provide an indication of the gene copy number of the methylated or unmethylated gene of interest (c) quantifying the results of the real-time detection against a standard curve for the methylated or unmethylated gene of interest to produce an output of gene copy number; characterised in that the amplification is considered valid where the cycle threshold value is less than 40.

It can be readily envisaged that the methods of the invention are equally useful in detecting the presence/amount of methylated or unmethylated versions of a gene in a DNA-containing sample. Detection of a methylated gene is more frequently utilised as a diagnostic indicator and thus, this represents the preferred application of the methods of the invention. However, for certain genes, detection of an unmethylated version of the gene may be of primary relevance.

The methods of the invention allow the presence of a methylated or unmethylated gene of interest to be detected in a sample in real-time. Since the methods of the invention are quantitative methods, the (relative) amounts of the methylated or unmethylated form of the gene of interest can also be determined as the reaction proceeds.

The methods of the invention are applicable to detecting the presence/amount of any gene of interest whose methylation status can usefully be determined. The methods have a range of diagnostic applications based upon the correlation between gene methylation and disease. Most preferably, the methylated or unmethylated gene of interest is MGMT. The MGMT gene encodes O6-methylguanine-DNA methyltransferase (MGMT), which is a cellular DNA repair protein that rapidly reverses alkylation (e.g. methylation) at the O6 position of guanine, thereby neutralizing the cytotoxic effects of alkylating agents such as temozolomide (TMZ) and carmustine (1-3). MGMT is the gene symbol approved by the HUGO Gene Nomenclature Committee. The gene is located on chromosome 10 (location 10q26) and the gene sequence is listed under the accession numbers M29971, NM_002412 and ENSG00000170430. Of course, as appropriate, the skilled person would appreciate that functionally relevant variants of the MGMT gene sequence may also be detected according to the methods of the invention. For example, the methylation status of a number of splice variants may be determined according to the methods of the invention. Variant sequences preferably have at least 90%, at least 91%, at least 92%, at least 93%, at least 94%, at least 95%, at least 96%, at least 97%, at least 98%, or at least 99% nucleotide sequence identity with the nucleotide sequences in the database entries. Computer programs for determining percentage nucleotide sequence identity are available in the art, including the Basic Local Alignment Search Tool (BLAST) available from the National Center for Biotechnology Information.

Other preferred genes, whose methylation status can be determined according to the methods of the invention, include WRN, BRCA1, PTEN and NDRG4. As shown in herein, the methylation status of these genes, to include variants as defined herein, can be reliably determined according to the methods of the invention.

WRN is the gene symbol approved by the HUGO Gene Nomenclature Committee. The gene is located on chromosome 8 (location p) and the gene sequence is listed under the accession number ENSG00000165392. The gene encodes the Werner syndrome associated DNA helicase from the RecQ family of helicases. Methylation of this gene may be linked to the incidence of colorectal cancer for example.

BRCA1 is the gene symbol approved by the HUGO Gene Nomenclature Committee. The gene is located on chromosome 17 (location q21-q24) and the gene sequence is listed under the accession numbers U14680 and ENSG00000012048. The gene encodes breast cancer 1, early onset which is one subunit of the BRCA1/BRCA2-containing complex. Methylation of this gene may be linked to the incidence of breast cancer for example.

PTEN is the gene symbol approved by the HUGO Gene Nomenclature Committee. The gene is located on chromosome 10 (location q23) and the gene sequence is listed under the accession numbers U92436, NM_000314 and ENSG00000171862. The gene encodes phosphatase and tensin homolog (mutated in multiple advanced cancers 1). Methylation of this gene may be linked to the incidence of a number of cancers, such as thyroid carcinomas (Alvarez-Nunez et al., Thyroid (2006) January; 16(1):17-23), melanoma (Mirmohammadsadegh et al., Cancer Res (2006); 66: (13) 6546-6552), Leukaemia (Lacayo et al., Clin Cancer Res (2006); 12(16) 4787-4789) and gynaecological cancers such as cervical and ovarian cancers (Yang et al., BMC Cancer (2006), 6:212) for example.

NDRG4 is the gene symbol approved by the HUGO Gene Nomenclature Committee. The gene is located on chromosome 16 (location q21-q22.3) and the gene sequence is listed under the accession numbers AB044947 and ENSG00000103034. The gene encodes NDRG family member 4. Methylation of this gene may be linked to the incidence of colorectal cancer for example.

Real-time methods do not need to be utilised, however. Analyses can be performed only to discover whether the target DNA is present in the sample or not. End-point amplification detection techniques utilize the same approaches as widely used for Real Time PCR. Therefore, the methods of the invention may encompass an end-point method of detecting the presence and/or amount of a methylated or unmethylated gene of interest in a DNA-containing sample. Thus, the invention provides a(n end point) method of detecting the presence and/or amount of a methylated or unmethylated gene of interest in a DNA-containing sample, comprising:

(a) contacting the DNA-containing sample with a reagent which selectively modifies unmethylated cytosine residues in the DNA to produce detectable modified residues but which does not modify methylated cytosine residues (b) amplifying at least a portion of the methylated or unmethylated gene of interest using at least one primer pair, at least one primer of which is designed to bind only to the sequence of methylated or unmethylated DNA following treatment with the reagent, wherein at least one primer in the primer pair is a primer containing a stem loop structure carrying a donor and an acceptor moiety of a molecular energy transfer pair arranged such that in the absence of amplification, the acceptor moiety quenches fluorescence emitted by the donor moiety (upon excitation) and during amplification, the stem loop structure is disrupted so as to separate the donor and acceptor moieties sufficiently to produce a detectable fluorescence signal which is detected at the end of the amplification to provide an indication of the gene copy number of the methylated or unmethylated gene of interest (c) quantifying the results of the detection against a standard curve for the methylated or unmethylated gene of interest to produce an output of gene copy number.

All embodiments of the invention are applicable to the end-point aspects of the invention and thus apply mutatis mutandis. End point analysis may invoke use of a fluorescent plate reader or other suitable instrumentation to determine the fluorescence at the end of the amplification.

It is noted that for each gene of interest, it may be possible to investigate methylation of the gene in a plurality of locations within the same gene. Thus, for example, a gene may incorporate more than one CpG island, or multiple sites within the same CpG island may be investigated as appropriate. Thus, panels of genes may be investigated in accordance with the present invention and may incorporate assessment of multiple sites within the same gene as appropriate.

The methods of the invention are most preferably ex vivo or in vitro methods carried out on any suitable (DNA containing) test sample. In one embodiment, however, the method may also include the step of obtaining the sample. The test sample is a DNA-containing sample, in particular a DNA-containing sample including the gene of interest. The methods of the invention can be used in the diagnosis of disease, in particular where methylation of a gene of interest is (known to be) linked to the incidence of disease. For example, methylation of a number of genes has been shown in the art to be correlated with the incidence of cancer. By selecting an appropriate gene of interest, the methods of the invention can thus be utilised in order to diagnose one or more cancer types. Examples include methylation of GSTPi for diagnosis of prostate cancer (for review on different prostate markers see Sperry et al., 2006); and methylation of GATA4 and many others for diagnosis of colorectal cancer (for review on CRC markers see Zitt et al., 2007).

The DNA-containing sample may comprise any suitable tissue sample or body fluid. Preferably, the test sample is obtained from a human subject. For cancer applications, the sample may comprise a tissue sample taken from the tissue suspected of being cancerous or from a representative bodily fluid. For example, in a preferred embodiment, where the gene of interest is MGMT, the sample may be a brain tissue sample or a cerebrospinal fluid sample. However, any other suitable test samples in which epigenetic silencing of the MGMT gene can be determined to indicate the presence of cancer are included within the scope of the invention.

Other DNA-containing sample for use in the methods of the invention include samples for diagnostic, prognostic, or personalised medicinal uses. These samples may be obtained from surgical samples, such as biopsies or fine needle aspirates, from paraffin embedded tissues, from frozen tumor tissue samples, from fresh tumour tissue samples or from a fresh or frozen body fluid, for example. Non-limiting examples include whole blood, bone marrow, cerebrospinal fluid, peritoneal fluid, pleural fluid, lymph fluid, serum, plasma, urine, chyle, stool, ejaculate, sputum, nipple aspirate, saliva, swabs specimens, colon wash specimens and brush specimens. The tissues and body fluids can be collected using any suitable method, many such methods are well known in the art. Assessment of a paraffin-embedded specimen can be performed directly or on a tissue section.

"Diagnosis" is defined herein to include screening for a disease or pre-indication of a disease, identifying a disease or pre-indication of a disease, monitoring the staging and the state and progression of the disease, checking for recurrence of disease following treatment and monitoring the success of a particular treatment. The methods of the invention may also have prognostic value, and this is included within the definition of the term "diagnosis". The prognostic value of the methods of the invention may be used as a marker of potential susceptibility to cancer or as a marker for progression from adenoma to cancer. Thus patients at risk may be identified before the disease has a chance to manifest itself in terms of symptoms identifiable in the patient.

The methods of the invention may be carried out on purified or unpurified DNA-containing samples. However, in a preferred embodiment, prior to step (a) (the reagent treatment step), DNA is isolated/extracted/purified from the DNA-containing sample. Any suitable DNA isolation technique may be utilised. Examples of purification techniques may be found in standard texts such as Molecular Cloning—A Laboratory Manual (Third Edition), Sambrook and Russell (see in particular Appendix 8 and Chapter 5 therein). In one preferred embodiment, purification involves alcohol precipitation of DNA. Preferred alcohols include ethanol and isopropanol. Suitable purification techniques also include salt-based precipitation methods. Thus, in one specific embodiment the DNA purification technique comprises use of a high concentration of salt to precipitate contaminants. The salt may comprise, consist essentially of or consist of potassium acetate and/or ammonium acetate for example. The method may further include steps of removal of contaminants which have been precipitated, followed by recovery of DNA through alcohol precipitation.

In an alternative embodiment, the DNA purification technique is based upon use of organic solvents to extract contaminants from cell lysates. Thus, in one embodiment, the method comprises use of phenol, chloroform and isoamyl alcohol to extract the DNA. Suitable conditions are employed to ensure that the contaminants are separated into the organic phase and that DNA remains in the aqueous phase. In preferred embodiments of these purification techniques, extracted DNA is recovered through alcohol precipitation, such as ethanol or isopropanol precipitation.

The methods of the invention may also, as appropriate, incorporate (also prior to step (a)) quantification of isolated/extracted/purified DNA in the sample. Quantification of the DNA in the sample may be achieved using any suitable means. Quantitation of nucleic acids may, for example, be based upon use of a spectrophotometer, a fluorometer or a UV transilluminator. Examples of suitable techniques are described in standard texts such as Molecular Cloning—A Laboratory Manual (Third Edition), Sambrook and Russell (see in particular Appendix 8 therein). In a preferred embodiment, kits such as the Picogreen® dsDNA quantitation kit available from Molecular Probes, Invitrogen may be employed to quantify the DNA.

The methods of the invention rely upon a reagent which selectively modifies unmethylated cytosine residues in the DNA to produce detectable modified residues. The reagent does not modify methylated cytosine residues and thus allows for discrimination between unmethylated and methylated nucleic acid molecules in a downstream process, preferably involving nucleic acid amplification. The reagent may, in one embodiment, act to selectively deaminate unmethylated cytosine residues. Thus, following exposure to the reagent the unmethylated DNA contains a different nucleotide sequence to that of corresponding methylated DNA. The deamination of cytosine results in a uracil residue being present, which has the same base pairing properties as thymine. Thus, the resultant sequence difference(s) may be detected in a number of ways—in this case through use of primers which bind to the methylated or unmethylated version of the sequence (including cytosine residues or uracil residues respectively). In a preferred embodiment, the reagent which selectively modifies unmethylated cytosine residues in the DNA to produce detectable modified residues but which does not modify methylated cytosine residues comprises, consists essentially of or consists of a bisulphite reagent (Frommer et al., Proc. Natl. Acad. Sci. USA 1992 89:1827-1831). Several bisulphite containing reagents are known in the art and suitable kits for carrying out the deamination reaction are commercially available (such as the EZ DNA methylation kit from Zymo Research). A particularly preferred reagent for use in the methods of the invention comprises, consists essentially of or consists of sodium bisulphite.

Once the DNA in the sample has been treated with the reagent, it is then necessary to detect the difference in nucleotide sequence caused by the reagent. This is done using a nucleic acid amplification technique. Functionally relevant methylation is most commonly associated with the promoter regions of genes. In particular, so called "CpG islands" include a relatively high incidence of CpG residues and are often found in the promoter region of the gene.

Thus, the methods of the invention typically focus on determining the presence of methylation in the CpG islands and/or promoters of the gene of interest. Various software programs exist to allow CpG islands in a gene of interest to be identified. Accordingly, the methods of the invention involve amplifying at least a portion of the methylated or unmethylated gene of interest using at least one primer pair. As discussed above, since the residues of interest whose methylation status is to be investigated, are typically found in defined CpG islands and/or in the promoter region of the gene of interest, the primer pair will typically amplify only a portion of the gene (in this region), rather than the entirety. Any suitable portion of the gene may be amplified according to the methods of the invention, provided that the amplification product is detectable as a reliable indicator of the presence of the gene of interest. Particularly readily detectable amplification products are between approximately 50 and 250 bp. Even more preferably, amplification using the at least one primer pair for amplification of the methylated or unmethylated gene of interest produces an amplification product of between approximately 100 and 200 bp. This is particularly relevant for tissue samples, especially paraffin embedded samples where limited DNA quality is typically obtained.

Short amplification products may also be advantageous in the context of plasma and serum samples where DNA of low molecular weight is predominant. Due to the lack of a requirement for a separate probe molecule, the methods of the invention are especially suitable for detecting such low molecular weight DNA molecules. Thus, the methods of the invention may alternatively be characterised by the fact that the portion of the methylated or unmethylated gene of interest which is amplified is between 50 and 250 bp, such as between 100 and 200 bp. The amplified product may be less than 200 bp and may be less than 150 bp, 125 bp, 110 bp or 100 bp in length. Such methods may be particularly applicable to plasma and serum samples, but may also be useful in the context of preserved tissue samples (such as paraffin embedded samples). In certain embodiments, the portion of the methylated or unmethylated gene of interest which is amplified is between approximately 50 and 200 bp, such as between 75 and 125 bp or between 80 and 110 bp in length. This may be applicable to any gene of interest and in the context of any disease indication. In certain embodiments, the gene is NDRG4. The disease may be colorectal cancer, where plasma and serum samples are diagnostically useful. Amplification of shorter lengths of DNA may equally be applied to the reference gene, as discussed herein.

At least one primer in the primer pair, and preferably both primers, is designed to bind only to the sequence of methylated or unmethylated DNA following treatment with the reagent. Thus, the primer acts to discriminate between a methylated and an unmethylated gene by base pairing only with the either the methylated form of the gene (which remains unmodified following treatment with the reagent) or the unmethylated form of the gene (which is modified by the reagent) depending upon the application to which the methods are put. The primer must, therefore, cover at least one methylation site in the gene of interest. Preferably, the primer binds to a region of the gene including at least 1, 2, 3, 4, 5, 6, 7 or 8 methylation sites. Most preferably the primer is designed to bind to a sequence in which all cytosine residues in CpG pairs within the primer binding site are methylated or unmethylated—i.e. a "fully methylated" or a "fully unmethylated" sequence. However, if only a single or a few methylation sites are of functional relevance, the primer may be designed to bind to a target sequence in which only these residues must be methylated (remain as a cytosine) or unmethylated (converted to uracil) for effective binding to take place. Other (non-functionally relevant) potential sites of methylation may be avoided entirely through appropriate primer design or primers may be designed which bind independently of the methylation status of these less relevant sites (for example by including a mix of G and A residues at the appropriate location within the primer sequence). Accordingly, an amplification product is expected only if the methylated or unmethylated form of the gene of interest was present in the original DNA-containing sample. Additionally or alternatively, it may be appropriate for at least one primer in the primer pair to bind only to the sequence of unmethylated DNA following treatment with the reagent and the other primer to bind to methylated DNA only following treatment—for example where a gene involves functionally important sites which are methylated and separate functionally important sites which are unmethylated.

At least one primer in the primer pair is a primer containing a stem loop or "hairpin" structure carrying a donor and an acceptor moiety of a molecular energy transfer pair. This primer may or may not be a primer which discriminates between methylated and unmethylated DNA as desired. The primer is arranged such that in the absence of amplification, the acceptor moiety quenches fluorescence emitted by the donor moiety upon excitation. Thus, prior to, or in the absence of, amplification directed by the primer the stem loop or "hairpin" structure remains intact. Fluorescence emitted by the donor moiety is effectively accepted by the acceptor moiety leading to quenching of fluorescence.

During amplification, the configuration of the stem loop or hairpin structure of the primer is altered. In particular, once the primer is incorporated into an amplification product, and in particular into a double stranded DNA, (particularly during the second round of amplification) the stem loop or hairpin structure is disrupted. This alteration in structure separates the donor and acceptor moieties sufficiently that the acceptor moiety is no longer capable of effectively quenching the fluorescence emitted by the donor moiety. Thus, the donor moiety produces a detectable fluorescence signal. This signal is detected in real-time to provide an indication of the gene copy number of the methylated or unmethylated gene of interest.

Thus, the methods of the invention utilise oligonucleotides for amplification of nucleic acids that are detectably labelled with molecular energy transfer (MET) labels. The primers contain a donor and/or acceptor moiety of a MET pair and are incorporated into the amplified product of an amplification reaction, such that the amplified product contains both a donor and acceptor moiety of a MET pair.

When the amplified product is double stranded, the MET pair incorporated into the amplified product may be on the same strand or, when the amplification is triamplification, on opposite strands. In certain instances wherein the polymerase used in amplification has 5'-3' exonuclease activity, one of the MET pair moieties may be cleaved from at least some of the population of amplified product by this exonuclease activity. Such exonuclease activity is not detrimental to the amplification methods of the invention.

The methods of the invention, as discussed herein are adaptable to many methods for amplification of nucleic acid sequences, including polymerase chain reaction (PCR), triamplification, and other amplification systems.

In a preferred embodiment, the MET is fluorescence resonance energy transfer (FRET), in which the oligonucleotides are labelled with donor and acceptor moieties, wherein the donor moiety is a fluorophore and the acceptor moiety may be a fluorophore, such that fluorescent energy emitted by the donor moiety is absorbed by the acceptor moiety. The acceptor moiety may be a quencher. Thus, the amplification primer is a hairpin primer that contains both donor and acceptor moieties, and is configured such that the acceptor moiety quenches the fluorescence of the donor. When the primer is incorporated into the amplification product its configuration changes, quenching is eliminated, and the fluorescence of the donor moiety may be detected.

The methods of the invention permit detection of an amplification product without prior separation of unincorporated oligonucleotides. Moreover, they allow detection of the amplification product directly, by incorporating the labelled oligonucleotide into the product.

In a preferred embodiment, the methods of the invention also involve determining the expression of a reference gene. Reference genes are important to allow comparisons to be made between different samples. By selecting an appropriate gene believed to be expressed in a stable and reliable fashion between the samples to be compared, detecting amplification of a reference gene together with the gene of interest takes into account inter-sample variability, such as amount of input material, enzymatic efficiency, sample degradation etc. A reference gene should ideally, in the presence of a reliable amount of input DNA, be one which is constantly expressed between the samples under test. Thus, the results from the gene of interest can be normalised against the corresponding copy number of the reference gene. Suitable reference genes for the present invention include beta-actin, glyceraldehyde-3-phosphate dehydrogenase (GAPDH), ribosomal RNA genes such as 18S ribosomal RNA and RNA polymerase II gene (Radonic A. et al., Biochem Biophys Res Commun. 2004 Jan. 23; 313(4):856-62). In a particularly preferred embodiment, the reference gene is beta-actin.

Thus the methods of the invention may be further characterised in amplifying at least a portion of a reference gene using at least one primer pair, wherein at least one primer in the primer pair is a primer containing a stem loop structure carrying a donor and an acceptor moiety of a molecular energy transfer pair arranged such that in the absence of amplification, the acceptor moiety quenches fluorescence emitted by the donor moiety (upon excitation) and during amplification, the stem loop structure is disrupted so as to separate the donor and acceptor moieties sufficiently to produce a detectable fluorescence signal which is detected, preferably in real-time, to provide an indication of the gene copy number of the reference gene.

Any suitable portion of the reference gene may be amplified according to the methods of the invention, provided that the amplification product is detectable as a reliable indicator of the presence of the reference gene. Particularly readily detectable amplification products are between approximately 50 and 250 bp. Even more preferably, amplification using the at least one primer pair for amplification of the reference gene produces an amplification product of between approximately 100 and 200 bp. This is particularly relevant for tissue samples, especially paraffin embedded samples where limited DNA quality is typically obtained.

In the embodiments in which a reference gene is included in the methods of the invention the methods may be further characterised in that the step of the methods which comprises quantifying the results of the (real-time) detection against a standard curve for the methylated or unmethylated gene of interest also comprises quantifying the results of the real-time detection of the reference gene against a standard curve for the reference gene to produce an output of gene copy number in each case and optionally further comprises normalising the results by dividing the gene copy number of the methylated or unmethylated gene of interest by the gene copy number of the reference gene. Again, the methods are characterised in that the amplification is considered valid where the cycle threshold value is less than 40. This is preferably the case for both the gene of interest and reference gene.

Amplification of at least a portion of the reference gene generally utilises at least one primer pair. Preferably, at least one primer in the primer pair is a primer containing a stem loop structure carrying a donor and an acceptor moiety of a molecular energy transfer pair, as for the gene of interest. The primer is arranged such that in the absence of amplification, the acceptor moiety quenches fluorescence emitted by the donor moiety upon excitation. Thus, prior to, or in the absence of, amplification directed by the primer the stem loop or "hairpin" structure remains intact. Fluorescence emitted by the donor moiety is effectively accepted by the acceptor moiety leading to quenching of fluorescence.

During amplification, the configuration of the stem loop or hairpin structure of the primer is altered. In particular, once the primer is incorporated into an amplification product, and in particular into a double stranded DNA, the stem loop or hairpin structure is disrupted. This alteration in structure separates the donor and acceptor moieties sufficiently that the acceptor moiety is no longer capable of effectively quenching the fluorescence emitted by the donor moiety. Thus, the donor moiety produces a detectable fluorescence signal. This signal is detected in real-time to provide an indication of the gene copy number of the reference gene. Alternatively, as discussed herein, the signal can be detected (solely) at the endpoint of the amplification.

The "hairpin" primers for use in the methods of the invention are most preferably as described in U.S. Pat. No. 6,090,552 and EP 0912597, the disclosures of which are hereby incorporated in their entirety. These primers are commercially known as Amplifluor® primers. Thus, in a particularly preferred embodiment, the primer containing a stem loop structure used to amplify a portion of the gene of interest and/or reference gene comprises, consists essentially of or consists of the following contiguous sequences in 5' to 3' order:

(a) a first nucleotide sequence of between approximately 6 and 30 nucleotides, wherein a nucleotide within said first nucleotide sequence is labelled with a first moiety selected from the donor moiety and the acceptor moiety of a molecular energy transfer pair, wherein the donor moiety emits fluorescence at one or more particular wavelengths when excited, and the acceptor moiety absorbs and/or quenches said fluorescence emitted by said donor moiety;

(b) a second, single-stranded nucleotide sequence comprising, consisting essentially of or consisting of between approximately 3 and 20 nucleotides;

(c) a third nucleotide sequence comprising, consisting essentially of or consisting of between approximately 6 and 30 nucleotides, wherein a nucleotide within said third nucleotide sequence is labelled with a second moiety selected from said donor moiety and said acceptor moiety, and said second moiety is the member of said group not labelling said first nucleotide sequence, wherein said third nucleotide sequence is complementary in reverse order to said first nucleotide sequence such that a duplex can form between said first nucleotide sequence and said third nucleotide sequence such that said first moiety and second moiety are in proximity such that, when the donor moiety is excited and emits fluorescence, the acceptor moiety absorbs and quenches said fluorescence emitted by said donor moiety; and (d) at the 3' end of the primer, a fourth, single-stranded nucleotide sequence comprising, consisting essentially of or consisting of between approximately 8 and 40 nucleotides that comprises at its 3' end a sequence complementary to a portion of the methylated or unmethylated DNA or reference gene and able to prime synthesis by a nucleic acid polymerase of a nucleotide sequence complementary to a nucleic acid strand comprising the portion of the methylated or unmethylated DNA or reference gene;

wherein when said duplex is not formed, said first moiety and said second moiety are separated by a distance that prevents molecular energy transfer between said first and second moiety.

In a particularly preferred embodiment, the donor moiety and acceptor moiety form a fluorescence resonance energy transfer (FRET) pair. Molecular energy transfer (MET) is a process by which energy is passed non-radiatively between a donor molecule and an acceptor molecule. Fluorescence resonance energy transfer (FRET) is a form of MET. FRET arises from the properties of certain chemical compounds; when excited by exposure to particular wavelengths of light, they emit light (i.e., they fluoresce) at a different wavelength. Such compounds are termed fluorophores. In FRET, energy is passed non-radiatively over a long distance (10-100 Å) between a donor molecule, which is a fluorophore, and an acceptor molecule. The donor absorbs a photon and transfers this energy non-radiatively to the acceptor (Förster, 1949, Z. Naturforsch. A4: 321-327; Clegg, 1992, Methods Enzymol. 211: 353-388). When two fluorophores whose excitation and emission spectra overlap are in close proximity, excitation of one fluorophore will cause it to emit light at wavelengths that are absorbed by and that stimulate the second fluorophore, causing it in turn to fluoresce. In other words, the excited-state energy of the first (donor) fluorophore is transferred by a resonance induced dipole-dipole interaction to the neighbouring second (acceptor) fluorophore. As a result, the lifetime of the donor molecule is decreased and its fluorescence is quenched, while the fluorescence intensity of the acceptor molecule is enhanced and depolarized. When the excited-state energy of the donor is transferred to a non-fluorophore acceptor, the fluorescence of the donor is quenched without subsequent emission of fluorescence by the acceptor. In this case, the acceptor functions as a quencher. Both quenchers and acceptors may be utilised in the present invention. Pairs of molecules that can engage in fluorescence resonance energy transfer (FRET) are termed FRET pairs. In order for energy transfer to occur, the donor and acceptor molecules must typically be in close proximity (up to 70 to 100 Å) (Clegg, 1992, Methods Enzymol. 211: 353-388; Selvin, 1995, Methods Enzymol. 246: 300-334). The efficiency of energy transfer falls off rapidly with the distance between the donor and acceptor molecules. According to Förster (1949, Z. Naturforsch. A4:321-327), the efficiency of energy transfer is proportional to $D \times 10^{-6}$, where D is the distance between the donor and acceptor. Effectively, this means that FRET can most efficiently occur up to distances of about 70 Å. Molecules that are commonly used in FRET include fluorescein, 5-carboxyfluorescein or 6-carboxyfluorescein (FAM), 2'7'-dimethoxy-4'5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo)benzoic acid (DABCYL), and 5-(2'-aminoethyl)aminonaphthalene-1-sulfonic acid (EDANS). Whether a fluorophore is a donor or an acceptor is defined by its excitation and emission spectra, and the fluorophore with which it is paired. For example, FAM is most efficiently excited by light with a wavelength of 488 nm, and emits light with a spectrum of 500 to 650 nm, and an emission maximum of 525 nm. FAM is a suitable donor fluorophore for use with JOE, TAMRA, and ROX (all of which have their excitation maximum at 514 nm).

Thus, in one embodiment, said donor moiety and said acceptor moiety are selected from 5-carboxyfluorescein or 6-carboxyfluorescein (FAM), 2'7'-dimethoxy-4'5'-dichloro-6-carboxyfluorescein (JOE), rhodamine, 6-carboxyrhodamine (R6G), N,N,N'-tetramethyl-6-carboxyrhodamine (TAMRA), 6-carboxy-X-rhodamine (ROX), 5-(2'-aminoethyl)aminonapthalene-1-sulfonic acid (EDANS), anthranilamide, coumarin, terbium chelate derivatives, Malachite green, Reactive Red 4, DABCYL, tetramethyl rhodamine, pyrene butyrate, eosine nitrotyrosine, ethidium, and Texas Red. In a further embodiment, said donor moiety is selected from fluorescein, 5-carboxyfluorescein or 6-carboxyfluorescein (FAM), rhodamine, 5-(2'-aminoethyl) aminonapthalene-1-sulfonic acid (EDANS), anthranilamide, coumarin, terbium chelate derivatives, Malachite green, and Reactive Red 4, and said acceptor moiety is selected from DABCYL, rhodamine, tetramethyl rhodamine, pyrene butyrate, eosine nitrotyrosine, ethidium, and Texas Red.

In one particularly preferred embodiment, said donor moiety is fluorescein or a derivative thereof, and said acceptor moiety is DABCYL. Preferably, the fluorescein derivative comprises, consists essentially of or consists of 6-carboxy fluorescein.

The MET labels can be attached at any suitable point in the primers. In a particularly preferred embodiment, the donor and acceptor moieties are positioned on complementary nucleotides within the stem loop structure, such that whilst the stem loop is intact, the moieties are in close physical proximity to one another. However, the primers of the invention may be labelled with the moieties in any position effective to allow MET/FRET between the respective donor and acceptor in the absence of amplification and separation of the donor and acceptor once the primer is incorporated into an amplification product.

The stem loop or hairpin structure sequence does not depend upon the nucleotide sequence of the target gene (gene of interest or reference gene) since it does not bind thereto. Accordingly, "universal" stem loop or hairpin sequences may be designed which can then be combined with a sequence specific primer to facilitate real-time detection of a sequence of interest. The main sequence requirement is that the sequence forms a stem loop/hairpin structure which is stable in the absence of amplification (and thus ensures efficient quenching). Thus, the sequence specific portion of the primer binds to a template strand and directs synthesis of the complementary strand. The primer therefore becomes part of the amplification product in the first round of amplification. When the complimentary strand is synthesised, amplification occurs through the stem loop/hairpin structure. This separates the fluorophore and quencher molecules, thus leading to generation of fluorescence as amplification proceeds.

A particularly preferred stem loop or hairpin structure for inclusion in primers for use in the methods of the invention comprises, consists essentially of or consists of the nucleotide sequence:

```
5' agcgatgcgttcgagcatcgcu    (SEQ ID NO: 1)
```

The stem loop structure is preferably found at the 5' end of the sequence specific portion of the primer used in the amplification.

As mentioned above, this detector sequence is generally labelled with a FRET pair. Preferably, one moiety in the FRET pair is found towards, near or at the 5'end of the sequence and the other moiety is found towards, near or at the 3'end of the sequence such that, when the stem loop or hairpin structure remains intact FRET is effective between the two moieties. In a particularly preferred embodiment, the stem loop or hairpin structure, especially the nucleic acid comprising, consisting essentially of or consisting of the sequence set forth as SEQ ID NO: 1, is labelled at the 5'end with FAM and at the 3'end with DABCYL. Other preferred combinations are discussed herein, which discussion applies mutatis mutandis.

As detailed in the experimental section, primers must be carefully selected in order to ensure sensitivity and specificity of the methods of the invention. Accordingly, particularly preferred primers for use in detecting methylated MGMT include a primer comprising, consisting essentially of or consisting of the nucleotide sequence set forth as:

```
5' tttcgacgttcgtaggttttcgc      (SEQ ID NO: 2)
``` and a primer comprising, consisting essentially of or consisting of the nucleotide sequence set forth as

```
5' ctcgaaactaccaccgtcccga      (SEQ ID NO: 3)
```

Either one or both of the primers may be labelled with or synthesised to incorporate a suitable stem loop or hairpin structure carrying a donor and acceptor moiety, preferably at the 5' end, as discussed in detail above. In a preferred embodiment, one or both of the primer(s) is labelled with or synthesised to incorporate, preferably at the 5' end, the stem loop structure comprising, consisting essentially of or consisting of the nucleotide sequence set forth as SEQ ID NO: 1. As mentioned above, this detector sequence is generally labelled with a FRET pair. Preferably, one moiety in the FRET pair is found towards, near or at the 5'end of the sequence and the other moiety is found towards, near or at the 3'end of the sequence such that, when the stem loop or hairpin structure remains intact FRET is effective between the two moieties. In a particularly preferred embodiment, the stem loop or hairpin structure, especially the nucleic acid comprising, consisting essentially of or consisting of the sequence set forth as SEQ ID NO: 1, is labelled at the 5'end with FAM and at the 3'end with DABCYL. Other preferred combinations are discussed herein, which discussion applies mutatis mutandis.

Particularly preferred primers for use in detecting the methylation status of BRCA1, in particular methylated BRCA1, include a primer comprising, consisting essentially of or consisting of one of the nucleotide sequences set forth in table 9, ie SEQ ID NO:6 or SEQ ID NO:13. Primer pairs can be readily selected from the primers set forth in table 9. Further combinations may be made as appropriate.

Either one or both of the primers in each primer pair may be labelled with or synthesised to incorporate a suitable stem loop or hairpin structure carrying a donor and acceptor moiety, preferably at the 5' end, as discussed in detail above. In a preferred embodiment, one or both of the primer(s) is labelled with or synthesised to incorporate, preferably at the 5' end, the stem loop structure comprising, consisting essentially of or consisting of the nucleotide sequence set forth as SEQ ID NO: 1. In table 9, the detector sequence (stem loop) is found on the forward primer. However, it may equally be found on the reverse primer if desired. Thus, the forward primer may comprise, consist essentially of or consist of the nucleotide sequence TCGTGGTAACGGAAAAGCGC (SEQ ID NO 6).

As mentioned above, the stem loop sequence is generally labelled with a FRET pair. Preferably, one moiety in the FRET pair is found towards, near or at the 5'end of the sequence and the other moiety is found towards, near or at the 3'end of the sequence such that, when the stem loop or hairpin structure remains intact FRET is effective between the two moieties. In a particularly preferred embodiment, the stem loop or hairpin structure, especially the nucleic acid comprising, consisting essentially of or consisting of the sequence set forth as SEQ ID NO: 1, is labelled at the 5'end with FAM and at the 3'end with DABCYL. Other preferred combinations are discussed herein, which discussion applies mutatis mutandis.

Particularly preferred primers for use in detecting the methylation status of WRN, in particular methylated WRN, include a primer comprising, consisting essentially of or consisting of one of the nucleotide sequences set forth in table 12, i.e. SEQ ID NO:14, SEQ ID NO:15, SEQ ID NO:16, SEQ ID NO:17, SEQ ID NO:18 or SEQ ID NO:19. Primer pairs can be readily selected from the primers set forth in table 12. Further combinations may be made as appropriate.

Either one or both of the primers in each primer pair may be labelled with or synthesised to incorporate a suitable stem loop or hairpin structure carrying a donor and acceptor moiety, preferably at the 5' end, as discussed in detail above. In a preferred embodiment, one or both of the primer(s) is labelled with or synthesised to incorporate, preferably at the 5' end, the stem loop structure comprising, consisting essentially of or consisting of the nucleotide sequence set forth as SEQ ID NO: 1. In table 12, the detector sequence (stem loop) is found on either the forward or reverse primer in each primer pair. However, it may equally be found on the other primer in each case, if desired.

As mentioned above, the stem loop sequence is generally labelled with a FRET pair. Preferably, one moiety in the FRET pair is found towards, near or at the 5'end of the sequence and the other moiety is found towards, near or at the 3'end of the sequence such that, when the stem loop or hairpin structure remains intact FRET is effective between the two moieties. In a particularly preferred embodiment, the stem loop or hairpin structure, especially the nucleic acid comprising, consisting essentially of or consisting of the sequence set forth as SEQ ID NO: 1, is labelled at the 5'end with FAM and at the 3'end with DABCYL. Other preferred combinations are discussed herein, which discussion applies mutatis mutandis.

Particularly preferred primers for use in detecting the methylation status of PTEN, in particular methylated PTEN, include a primer comprising, consisting essentially of or consisting of one of the nucleotide sequences set forth in table 16, i.e. SEQ ID NO:20, SEQ ID NO:21, SEQ ID NO:22, SEQ ID NO:23, SEQ ID NO:24 or SEQ ID NO:25. Primer pairs can be readily selected from the primers set forth in table 16. Further combinations may be made as appropriate.

Either one or both of the primers in each respective primer pair may be labelled with or synthesised to incorporate a suitable stem loop or hairpin structure carrying a donor and acceptor moiety, preferably at the 5' end, as discussed in detail above. In a preferred embodiment, one or both of the primer(s) is labelled with or synthesised to incorporate, preferably at the 5' end, the stem loop structure comprising, consisting essentially of or consisting of the nucleotide sequence set forth as SEQ ID NO: 1. In table 16, the detector sequence (stem loop) is found on the forward primer. However, it may equally be found on the reverse primer if desired. Thus, the forward primer may lack the stem loop structure in this case.

As mentioned above, the stem loop sequence is generally labelled with a FRET pair. Preferably, one moiety in the FRET pair is found towards, near or at the 5'end of the sequence and the other moiety is found towards, near or at the 3'end of the sequence such that, when the stem loop or hairpin structure remains intact FRET is effective between the two moieties. In a particularly preferred embodiment, the stem loop or hairpin structure, especially the nucleic acid comprising, consisting essentially of or consisting of the sequence set forth as SEQ ID NO: 1, is labelled at the 5'end with FAM and at the 3'end with DABCYL. Other preferred combinations are discussed herein, which discussion applies mutatis mutandis.

Particularly preferred primers for use in detecting the methylation status of NDRG4, in particular methylated NDRG4, include a primer comprising, consisting essentially of or consisting of one of the nucleotide sequences set forth in table 18, i.e. SEQ ID NO:26, SEQ ID NO:27, SEQ ID NO:28, SEQ ID NO:29, SEQ ID NO:30, SEQ ID NO:31, SEQ ID NO:32 or SEQ ID NO:33. Primer pairs can be readily selected from the primers set forth in table 18. Further combinations may be made as appropriate.

Either one or both of the primers in each primer pair may be labelled with or synthesised to incorporate a suitable stem loop or hairpin structure carrying a donor and acceptor moiety, preferably at the 5' end, as discussed in detail above. In a preferred embodiment, one or both of the primer(s) is labelled with or synthesised to incorporate, preferably at the 5' end, the stem loop structure comprising, consisting essentially of or consisting of the nucleotide sequence set forth as SEQ ID NO: 1. In table 18, the detector sequence (stem loop) is found on either the forward or reverse primer in each primer pair. However, it may equally be found on the other primer in each case, if desired.

As mentioned above, the stem loop sequence is generally labelled with a FRET pair. Preferably, one moiety in the FRET pair is found towards, near or at the 5'end of the sequence and the other moiety is found towards, near or at the 3'end of the sequence such that, when the stem loop or hairpin structure remains intact FRET is effective between the two moieties. In a particularly preferred embodiment, the stem loop or hairpin structure, especially the nucleic acid comprising, consisting essentially of or consisting of the sequence set forth as SEQ ID NO: 1, is labelled at the 5'end with FAM and at the 3'end with DABCYL. Other preferred combinations are discussed herein, which discussion applies mutatis mutandis.

Also provided by the present invention are primers for real time amplification and detection of the preferred reference gene, beta-actin. Preferred primers include a primer comprising, consisting essentially of or consisting of the nucleotide sequence set forth as:

```
5' tagggagtatataggttggggaagtt    (SEQ ID NO: 4)
``` and a primer comprising, consisting essentially of or consisting of the nucleotide sequence set forth as

```
5' aacacacaataacaaacacaaattcac  (SEQ ID NO: 5)
```

Either one or both of the primers may be labelled with or synthesised to incorporate a suitable stem loop or hairpin structure carrying a donor and acceptor moiety, preferably at the 5' end, as discussed in detail above. In a preferred embodiment, one or both of the primer(s) is labelled, or synthesised to incorporate preferably at the 5' end, with the stem loop structure comprising, consisting essentially of or consisting of the nucleotide sequence set forth as SEQ ID NO: 1. As mentioned above, this detector sequence is generally labelled with a FRET pair. Preferably, one moiety in the FRET pair is found towards, near or at the 5'end of the sequence and the other moiety is found towards, near or at the 3'end of the sequence such that, when the stem loop or hairpin structure remains intact FRET is effective between the two moieties. In a particularly preferred embodiment, the stem loop or hairpin structure, especially the nucleic acid comprising, consisting essentially of or consisting of the sequence set forth as SEQ ID NO: 1, is labelled at the 5'end with FAM and at the 3'end with DABCYL. Other preferred combinations are discussed herein, which discussion applies mutatis mutandis.

These primers and hairpin structures form separate aspects of the present invention. Further characteristics of these primers and hairpin structures are summarized in the detailed description (experimental part) below. It is noted that variants of these sequences may be utilised in the present invention. In particular, additional flanking sequences may be added, for example to improve binding specificity or the formation of a stem loop, as required. Variant sequences preferably have at least 90%, at least 91%, at least 92%, at least 93%, at least 94%, at least 95%, at least 96%, at least 97%, at least 98%, or at least 99% nucleotide sequence identity with the nucleotide sequences of the primers and/or probes set forth in SEQ ID NO:1 to 33 and in the relevant tables. The primers and hairpin structures may incorporate synthetic nucleotide analogues as appropriate or may be DNA, RNA or PNA based for example, or mixtures thereof. Similarly alternative fluorescent donor and acceptor moieties/FRET pairs may be utilised as appropriate. In addition to being labelled with the fluorescent donor and acceptor moieties, the primers may include modified oligonucleotides and other appending groups and labels provided that the functionality as a primer and/or stem loop/hairpin structure in the methods of the invention is not compromised.

For each primer pair at least one primer is labelled with a donor and an acceptor moiety of a molecular energy transfer pair arranged such that in the absence of amplification, the acceptor moiety quenches fluorescence emitted by the donor moiety (upon excitation) and during amplification, the stem loop structure is disrupted so as to separate the donor and acceptor moieties sufficiently to produce a detectable fluorescence signal which is detected in real-time to provide an indication of the gene copy number of the methylated MGMT or beta-actin gene. Preferably, said donor moiety and said acceptor moiety are a FRET pair. In one embodiment, said donor moiety and said acceptor moiety are selected from 5-carboxyfluorescein or 6-carboxyfluorescein (FAM), 2'7'-dimethoxy-4'5'-dichloro-6-carboxyfluorescein (JOE), rhodamine, 6-carboxyrhodamine (R6G), N,N,N'-tetramethyl-6-carboxyrhodamine (TAMRA), 6-carboxy-X-rhodamine (ROX), 5-(2'-aminoethyl)aminonapthalene-1-sulfonic acid (EDANS), anthranilamide, coumarin, terbium chelate derivatives, Malachite green, Reactive Red 4, DABCYL, tetramethyl rhodamine, pyrene butyrate, eosine nitrotyrosine, ethidium, and Texas Red. In a further embodiment, said donor moiety is selected from fluorescein, 5-carboxyfluorescein or 6-carboxyfluorescein (FAM), rhodamine, 5-(2'-aminoethyl)aminonapthalene-1-sulfonic acid (EDANS), anthranilamide, coumarin, terbium chelate derivatives, Malachite green, and Reactive Red 4, and said acceptor moiety is selected from DABCYL, rhodamine, tetramethyl rhodamine, pyrene butyrate, eosine nitrotyrosine, ethidium, and Texas Red. Preferably, said donor moiety is fluorescein or a derivative thereof, and said acceptor moiety is DABCYL and most preferably the donor moiety is 6-carboxyfluorescein. Other preferred combinations, particularly in a multiplexing context, are discussed herein and these combinations are also envisaged for these aspects of the invention.

Particularly preferred primer pairs are:

```
Forward Primer MGMT:
                        (SEQ ID NO: 1 plus SEQ ID NO: 2)
5'-agcgatgcgttcgagcatcgcutttcgacgttcgtaggttttcgc Reverse Primer MGMT:
                                       (SEQ ID NO: 3)
5'-ctcgaaactaccaccgtcccga Forward Primer beta-actin:
                        (SEQ ID NO: 1 plus SEQ ID NO: 4)
5'-agcgatgcgttcgagcatcgcutagggagtatataggttggggaagtt
```

-continued

Reverse Primer beta-actin:
(SEQ ID NO: 5)
5'-aacacacaataacaaacacaaattcac

However, the stem loop (or another suitable stem loop/hairpin structure) may be incorporated (preferably during oligonucleotide synthesis) into the reverse primer in each case in an alternative embodiment.

The invention also provides kits which may be used in order to carry out the methods of the invention. The kits may incorporate any of the preferred features mentioned in connection with the various methods (and uses) of the invention described herein. Thus, the invention provides a kit for detecting the presence and/or amount of a methylated or unmethylated gene of interest in a DNA-containing sample, comprising at least one primer pair of the invention. In particular, the invention provides a kit for real-time detection of the (methylated) MGMT gene comprising at least one primer pair of the invention. Preferably, the kit incorporates a primer pair of the invention for detecting the presence and/or amount of methylated MGMT and a primer pair for detecting the presence and/or amount of a reference gene, in particular beta-actin. Thus, the kit may comprise primer pairs comprising a primer comprising, consisting essentially of or consisting of the nucleotide sequence set forth as SEQ ID NO:2/3/7/8/9/10/11/12. The kit preferably includes primer pairs comprising, consisting essentially of or consisting of the nucleotide sequence set forth as SEQ ID NOs 2 and 3 since this primer pair was shown experimentally to be most effective in the methods of the invention. Preferably, at least one primer in each primer pair is labelled with an appropriate stem loop or hairpin structure to facilitate detection in real-time, as discussed above (which discussion applies here mutatis mutandis). Most preferably at least one primer in each primer pair incorporates the stem loop or hairpin structure which comprises, consists essentially of or consists of the nucleotide sequence set forth as SEQ ID NO:1. The stem loop structure is labelled with an appropriate donor and acceptor moiety, as discussed herein (which discussion applies here mutatis mutandis).

As aforementioned, further characteristics of the primers of the invention are summarized in the detailed description (experimental part) below. Variants of these sequences may be utilised in the present invention as discussed herein. Alternative fluorescent donor and acceptor moieties/FRET pairs may be utilised as appropriate, as discussed herein. Related kits are also envisaged for the WRN (table 12—SEQ ID NO:14, SEQ ID NO:15, SEQ ID NO:16, SEQ ID NO:17, SEQ ID NO:18 or SEQ ID NO:19), BRCA1 (table 9—SEQ ID NO:6 and/or 13), PTEN (table 16—SEQ ID NO:20, SEQ ID NO:21, SEQ ID NO:22, SEQ ID NO:23, SEQ ID NO:24 or SEQ ID NO:25) and NDRG4 (table 18—SEQ ID NO:26, SEQ ID NO:27, SEQ ID NO:28, SEQ ID NO:29, SEQ ID NO:30, SEQ ID NO:31, SEQ ID NO:32 or SEQ ID NO:33) genes incorporating suitable primer pairs as described herein.

In one embodiment, the kit of the invention further comprises a reagent which modifies unmethylated cytosine, as discussed herein. Such a reagent is useful for distinguishing methylated from unmethylated cytosine residues. In a preferred embodiment, the reagent comprises bisulphite, preferably sodium bisulphite. This reagent is capable of converting unmethylated cytosine residues to uracil, whereas methylated cytosines remain unconverted. This difference in residue may be utilised to distinguish between methylated and unmethylated nucleic acid in a downstream process, such as PCR using primers which distinguish between cytosine and uracil (cytosine pairs with guanine, whereas uracil pairs with adenine).

As discussed with respect to the methods of the invention herein, suitable controls may be utilised in order to act as quality control for the methods. Accordingly, in one embodiment, the kit of the invention further comprises, consists essentially of or consists of one or more control nucleic acid molecules of which the methylation status is known. For the MGMT gene, these control nucleic acids may be derived from SW48 cells and/or HT29 cells. These (one or more) control nucleic acid molecules may include both nucleic acids which are known to be, or treated so as to be, methylated and/or nucleic acid molecules which are known to be, or treated so as to be, unmethylated. One example of a suitable internal reference gene, which is generally unmethylated, but may be treated so as to be methylated, is beta-actin.

The kits of the invention may additionally include suitable buffers and other reagents for carrying out the claimed methods of the invention. Thus, the discussion provided in respect of the methods of the invention applies mutatis mutandis here and is not repeated for reasons of conciseness. In one embodiment, the kit of the invention further comprises, consists essentially of, or consists of nucleic acid amplification buffers.

The kit may also additionally comprise, consist essentially of or consist of enzymes to catalyze nucleic acid amplification. Thus, the kit may also additionally comprise, consist essentially of or consist of a suitable polymerase for nucleic acid amplification. Examples include those from both family A and family B type polymerases, such as Taq, Pfu, Vent etc.

The various components of the kit may be packaged separately in individual compartments or may, for example be stored together where appropriate.

The kit may also incorporate suitable instructions for use, which may be printed on a separate sheet or incorporated into the kit's packaging for example. The instructions may facilitate use of the kits of the invention with an appropriate real-time amplification apparatus, a number of which are commercially available.

The last step of the real-time methods of the invention involves quantifying the results of the real-time detection against a standard curve for the methylated or unmethylated gene of interest, and optionally the reference gene (where included). Standard curves may be generated using a set of standards. Each standard contains a known copy number, or concentration, of the gene of interest and/or reference gene as appropriate. Typically, a baseline value of fluorescence will be set to account for background fluorescence. For example, in one embodiment the Sequence Detection System (SDS) software is utilised. This software sets a default baseline range of cycles 3 to 15 of the amplification reaction before amplification products are detected. A threshold value of fluorescence is then defined at a statistically significant value above this baseline. Typically, the threshold is set to 10 standard deviations above the baseline fluorescence. Appropriate software is provided with apparatus for carrying out real-time amplification reactions. The software automatically calculates the baseline and threshold values for the reaction. The threshold cycle value (Ct) can then be determined for each standard. This is the number of cycles required to achieve the threshold amplification level. Thus, the greater the initial concentration of the gene standard in the reaction mixture, the fewer the number of cycles required to achieve a particular yield of amplified product. A plot of Ct against the $\log_{10}$ of the known initial copy number of the set of standard DNAs produces a straight line. This is the standard curve. Thus, the Ct value for the amplification of the gene of interest and reference gene, where utilised, can each be interpolated against the respective standard curve in order to determine the copy number in the DNA-containing sample. Thus, the output of the method is the gene copy number for each of the gene of interest and reference gene. The results may be normalised by dividing the gene copy number of the methylated or unmethylated gene of interest by the gene copy number of the reference gene. In a preferred embodiment, the Applied Biosystems 7900 HT fast real-time PCR system is used to carry out the methods of the invention. Preferably, SDS software is utilised, preferably including a suitable algorithm such as the Auto CT algorithm for automatically generating baseline and threshold values for individual detectors.

As discussed in the experimental section, whilst the use of a real-time amplification method involving primers only (i.e. does not require the presence of a separate probe) provides certain technical advantages (as discussed in U.S. Pat. No. 6,090,552 and EP 0912597), there is the problem to solve of non-specific amplification. The selection of appropriate primers helps to improve specificity and the usefulness of the primers can be determined by selecting an appropriate Ct value which defines whether the amplification should be considered a valid reaction. For the purposes of the methods of the invention, it has been found that if the amplification is only considered valid where the cycle threshold value is less than (or equal to) around 40 (such as 35 to 45, or 37 to 43, or 38 to 42 or 39 to 41), sensitive and specific results can be obtained. If the threshold is only crossed after more than 40 cycles, the amplification is considered invalid and the results are not utilised.

Whilst selection of a Ct value of less than 40 for the gene of interest and optionally also for the reference gene (where included) represents the primary validation criterion, additional validation criteria may also be utilised in the methods of the invention. Thus, in one embodiment the amplification is considered valid where the slope of the standard curve for the methylated or unmethylated gene of interest and reference gene is at least −4, indicating an amplification efficiency of at least 77%.

In a further embodiment, the amplification is considered valid where the coefficient of determination ($R^2$) for at least four data points on each curve is above 0.990.

In a still further embodiment, the amplification is considered valid where, in a parallel reaction using the same reagents, there is no amplification of a sample containing no DNA at the cycle threshold value of less than 40. Any suitable sample lacking a DNA component, such as a water sample for example, may be utilised.

In a yet further embodiment, the amplification is considered valid where, in a parallel reaction using the same reagents, there is detectable amplification of a positive control sample known to contain the gene of interest in methylated form at the cycle threshold value of less than 40. Any suitable positive control sample may be utilised. As an example, where the gene of interest is MGMT the positive control sample known to contain methylated MGMT is preferably derived from SW48 cells.

A further validation criterion comprises the amplification being considered valid where, in a parallel reaction using the same reagents, there is no detectable amplification of a negative control sample known to contain the gene of interest in unmethylated form at the cycle threshold value of less than 40. Any suitable negative control sample may be utilised. As an example, where the gene of interest is MGMT the negative control sample known to contain unmethylated MGMT is preferably derived from HT29 cells.

Once the output of gene copy number has been obtained the method may further comprise carrying out a statistical analysis of the results obtained. For example, density plots of the results obtained may be generated to provide an indication of the distribution of results. $Log_2$ transformation may be utilised to produce density plots and also assess the reproducibility of the methods by a direct comparison of duplicate experiments. Cohen's Kappa values may be calculated to provide an indication of the reproducibility of the methods (through comparison of results obtained through duplicate experiments or by comparing results obtained with the claimed methods with other known methods). Receiver Operating Characteristics (ROC) curves may be plotted to determine the specificity (proportion of true negative results) and sensitivity (proportion of true positive results) of the methods. The area under the ROC curve (AUC) provides an indication of the overall performance of the method. Preferably, the AUC is at least 0.90, 0.91, 0.92, 0.93, 0.94, 0.95, 0.96, 0.97, 0.98 or 0.99 for the methods of the invention. In one embodiment, the software environment R is utilised to carry out the analysis.

Whilst suitable reaction conditions can be determined by one skilled in the art, it has been found that certain primer concentrations work effectively in the methods of the invention. Accordingly, in one embodiment, the at least one primer pair for amplification of the methylated or unmethylated gene of interest/reference gene is used in the amplification at a concentration of approximately 50 to 150 nM. More preferably, the at least one primer pair for amplification of the methylated or unmethylated gene of interest/reference gene is used in the amplification at a concentration of approximately 100 nM.

Whilst the methods of the invention may be utilised with any suitable amplification technique, it is most preferred that amplification is carried out using the polymerase chain reaction (PCR). Thus, whilst PCR is a preferred amplification method, to include variants on the basic technique such as nested PCR, equivalents may also be included within the scope of the invention. Examples include, without limitation, isothermal amplification techniques such as NASBA, 3SR, TMA and triamplification, all of which are well known in the art and suitable reagents are commercially available. Other suitable amplification methods include, without limitation, the ligase chain reaction (LCR) (Barringer et al, 1990), MLPA, selective amplification of target polynucleotide sequences (U.S. Pat. No. 6,410,276), consensus sequence primed polymerase chain reaction (U.S. Pat. No. 4,437,975), invader technology (Third Wave Technologies, Madison, Wis.), strand displacement technology, arbitrarily primed polymerase chain reaction (WO90/06995) and nick displacement amplification (WO2004/067726).

The real-time PCR methods of the invention generally involve steps of lowering the temperature to allow primer annealing, raising the temperature for primer extension, raising the temperature for denaturation and lowering the temperature for data-collection. In one specific embodiment, the data-collection step is carried out at a temperature of between approximately 60° C. and 64° C., most preferably at approximately 62° C. since this has been shown to give maximally sensitive and specific results (as discussed in Example 2 below). Data collection may be carried out at 57° C. in certain embodiments. Data collection may be carried out for a suitable period of time, such as 30 seconds or 1 minute per cycle.

Annealing temperatures may be varied as would be appreciated by one skilled in the art, depending upon the primers utilised in the reaction. Suitable annealing temperatures herein may be between 50° C. and 90° C. Particularly useful annealing temperatures have been shown to be between 55° C. and 65° C., especially 57° C. and/or 62° C. These annealing temperatures may be used for any gene of interest, as indicated herein.

In a specific embodiment, the thermal profiling of the polymerase chain reaction comprises between 40 and 50 repeats, preferably approximately 45 repeats of the cycle:
(a) approximately 50° C. for approximately 2 minutes
(b) approximately 95° C. for approximately 10 minutes
(c) approximately 95° C. for approximately 15 seconds
(d) approximately 62° C. for approximately 1 minute This reaction scheme has been shown to produce specific and sensitive results in the methods of the invention. Alternative thermal profiles are discussed in the experimental section and may be applied as appropriate.

It is possible for the methods of the invention to be used in order to detect more than one gene of interest in the same reaction. Through the use of several specific sets of primers, amplification of several nucleic acid targets can be performed in the same reaction mixture. This may be termed "multiplexing". In a preferred embodiment, one or both primers for each target may be hairpin primers labelled with a fluorescent moiety and a quenching moiety that form a FRET pair. Amplification of several nucleic acid targets requires that a different fluorescent donor and/or acceptor moiety, with a different emission wavelength, be used to label each set of primers. During detection and analysis after an amplification, the reaction mixture is illuminated and read at each of the specific wavelengths characteristic for each of the sets of primers used in the reaction. It can thus be determined which specific target DNAs in the mixture were amplified and labelled. In a specific embodiment, two or more primer pairs for amplification of different respective target sequences are used. Thus the presence and/or amount of a panel of methylated/unmethylated genes of interest can be detected in a single DNA-containing sample Multiplexing can also be utilised in the context of detecting both the gene of interest and a reference gene in the same reaction. Again, primers labelled with appropriate distinguishable donor and/or acceptor moieties allow the signal generated by amplification of the gene of interest and reference gene respectively to be distinguished.

In one embodiment, a universal quencher is utilised together with suitable fluorophore donors each having a distinguishable emission wavelength maximum. A particularly preferred quencher is DABCYL. Together with DABCYL as quencher, the following fluorophores may each be utilised to allow multiplexing: Coumarin (emission maximum of 475 nm), EDANS (491 nm), fluorescein (515 nm), Lucifer yellow (523 nm), BODIPY (525 nm), Eosine (543 nm), tetramethylrhodamine (575 nm) and texas red (615 nm) (Tyagi et al., Nature Biotechnology, Vol. 16, January 1998; 49-53). Other preferred combinations are discussed herein.

In an alternative embodiment, the DNA-containing sample can be split and the methods of the invention carried out on suitable portions of the sample in order to obtain directly comparable results. Thus, where both the gene of interest and a reference gene are detected, the sample may be split two ways to allow detection of amplification of the gene of interest in real time in one sample portion and detection of amplification of the reference gene in real time in the other sample portion. The sample may be split further to allow suitable control reactions to be carried out, as required. The benefit of this scheme is that a universal FRET pair can be used to label each primer pair and removes the requirement to detect emission at a range of wavelengths. However, this method does rely upon obtaining a suitable sample initially to permit dividing the sample. Whilst any suitable reaction volume may be utilised, in one specific embodiment, the total reaction volume for the amplification step is between approximately 10 and 40 μl, more preferably between approximately 20 and 30 μl and most preferably around 25 μl.

As mentioned above, epigenetic silencing of the MGMT gene has been shown to correlate with improved survival in several studies with glioma patients treated with alkylating agent therapy (7) and has been substantiated in two clinical trials (8, 9). The methylation status of MGMT is believed to have a predictive value for benefit from the addition of the alkylating agent TMZ (9, 10). Hence, this epigenetic alteration in tumors can be exploited in a diagnostic test to predict benefit from alkylating agent therapy for individualized management of patients. Beside glioblastoma, there is a published report that the MGMT methylation status may also predict benefit from alkylating agent containing therapy in patients with low grade glioma, oligodendroglioma, and diffuse large B-cell lymphoma.

Accordingly, in a further aspect the invention provides a method of predicting the likelihood of successful treatment of a cell proliferative disorder in a subject using an alkylating chemotherapeutic agent comprising, in a DNA-containing sample isolated from the subject, detecting the presence and/or amount of methylated MGMT gene in the sample by carrying out a method of the invention, wherein the presence of methylated MGMT in the sample indicates that the likelihood of successful treatment using the alkylating chemotherapeutic agent is higher than if no or lower levels of methylated MGMT is detected. Of course, the reverse situation is also applicable and so the methods of the invention may likewise be utilised in order to determine whether there is likely to be resistance to, or unsuccessful treatment using, an alkylating chemotherapeutic agent—the absence of methylated MGMT in the sample indicates there is likely to be resistance to treatment and/or that treatment is likely to be unsuccessful. Thus, the methods of the invention may also be utilised to select a suitable course of treatment for a patient—the presence of methylated MGMT indicates alkylating agents may be beneficially administered, whereas the absence or low level of methylated MGMT indicates alkylating agents are contra-indicated. The discussion provided in respect of the methods, primers and kits of the invention applies to the present aspect mutatis mutandis and all embodiments are therefore envisaged, as appropriate, for this aspect of the invention.

In a preferred embodiment, the cell proliferative disorder is cancer. Preferably, the cancer is cancer of the central nervous system and especially the brain. In a specific embodiment, the cancer of the brain comprises, consists essentially of or consists of a glioma. Preferably, the glioma comprises, consists essentially of or consists of a glioblastoma or oligodendroglioma. In an alternative embodiment, the cell proliferative disorder is diffuse large B-cell lymphoma.

The alkylating agent may be any suitable agent useful for treating a cellular proliferative disorder. Preferably, the alkylating chemotherapeutic agent is selected from carmustine, lomustine, cisplatin, carboplatin, mechlorethamine, cyclophosphamide, ifosfamide, melphalan, chlorambucil, busulfan, thiotepa, dacarbazine, temozolamide or procarbazine. All of these agents are known in the art.

Methylation of MGMT, WRN, BRCA1, PTEN and NDRG4 appears to be linked to certain cancer types. Accordingly, in a specific embodiment, the invention provides a method of detecting a predisposition to, or the incidence of, cancer of the central nervous system and especially the brain or diffuse large B cell lymphoma in a sample comprising detecting methylation of the MGMT gene using the methods of the invention, wherein detection of methylation is indicative of a predisposition to, or the incidence of, cancer and in particular cancer of the central nervous system and especially the brain or diffuse large B cell lymphoma. Corresponding methods are envisaged for WRN and colorectal cancer, BRCA1 and breast cancer, NDRG4 and colorectal cancer and PTEN and cancers such as thyroid carcinomas, melanoma, Leukaemia and gynaecological cancers such as cervical and ovarian cancers.

In a related embodiment, the invention provides a method for determining the histopathological stage of cancer of the central nervous system and especially the brain or diffuse large B cell lymphoma in a sample comprising detecting methylation of the MGMT gene using the methods of the invention, wherein detection of methylation is indicative of the histopathological stage of the cancer of the central nervous system and especially the brain or diffuse large B cell carcinoma. All embodiments of the methods of the invention are hereby incorporated as appropriate and are not repeated for reasons of conciseness. The "stage" of a cancer is a descriptor (usually numbers I to IV) of how much the cancer has spread. The stage often takes into account the size of a tumour, how deep it has penetrated, whether it has invaded adjacent organs, if and how many lymph nodes it has metastasized to, and whether it has spread to distant organs. Staging of cancer is important because the stage at diagnosis is the biggest predictor of survival, and treatments are often changed based on the stage. Again, corresponding methods are envisaged for WRN and colorectal cancer, BRCA1 and breast cancer, NDRG4 and colorectal cancer and PTEN and cancers such as thyroid carcinomas, melanoma, Leukaemia and gynaecological cancers such as cervical and ovarian cancers.

Testing can be performed diagnostically or in conjunction with a therapeutic regimen. Epigenetic loss of function of the MGMT gene can be rescued by the use of DNA demethylating agents and/or DNA methyltransferase inhibitors. Testing can be used to determine what therapeutic or preventive regimen to employ on a patient and be used to monitor efficacy of a therapeutic regimen.

Accordingly, in one embodiment, the methods of the invention are applied in a method for predicting the likelihood of successful treatment of cancer of the central nervous system and especially the brain or diffuse large B cell lymphoma with a DNA demethylating agent and/or a DNA methyltransferase inhibitor and/or HDAC inhibitor comprising detecting methylation of the MGMT gene using the methods of the invention, wherein detection of methylation is indicative that the likelihood of successful treatment is higher than if the epigenetic modification is not detected.

In an opposite scenario, the invention provides for a method for predicting the likelihood of resistance to treatment of cancer of the central nervous system and especially the brain or diffuse large B cell lymphoma with a DNA demethylating agent and/or a DNA methyltransferase inhibitor and/or HDAC inhibitor comprising detecting methylation of the MGMT gene using the methods of the invention, wherein detection of methylation is indicative that the likelihood of resistance to treatment is lower than if the epigenetic modification is not detected.

Thus, the patient population may be selected for treatment on the basis of their methylation status with respect to the MGMT gene. This leads to a much more focussed and personalised form of medicine and thus leads to improved success rates since patients will be treated with drugs which are most likely to be effective.

Once again, corresponding methods are envisaged for WRN and colorectal cancer, BRCA1 and breast cancer, NDRG4 and colorectal cancer and PTEN and cancers such as thyroid carcinomas, melanoma, Leukaemia and gynaecological cancers such as cervical and ovarian cancers.

The invention further provides for a method of selecting a suitable treatment regimen for cancer of the central nervous system and especially the brain or diffuse large B cell lymphoma comprising detecting methylation of the MGMT gene using the methods of the invention, wherein detection of methylation results in selection of a DNA demethylating agent and/or a DNA methyltransferase inhibitor and/or a HDAC inhibitor for treatment and wherein if methylation is not detected, a DNA demethylating agent and/or a DNA methyltransferase inhibitor and/or a HDAC inhibitor is not selected for treatment. In the event that methylation is not detected, alternative treatments should be explored.

In another aspect, the invention provides for a method of treating cancer and in particular cancer of the central nervous system and especially the brain or diffuse large B cell lymphoma comprising administration of a DNA demethylating agent and/or a HDAC inhibitor and/or a DNA methyltransferase inhibitor wherein the subject has been selected for treatment using the methods of the invention. Thus, for the patient population where the MGMT gene is methylated, which leads to decreased gene expression, this type of treatment is recommended.

In a related aspect, the invention also provides for the use of a DNA demethylating agent and/or a DNA methyltransferase inhibitor and/or HDAC inhibitor (in the manufacture of a medicament for use) in treating cancer of the central nervous system and especially the brain or diffuse large B cell lymphoma in a subject, wherein the subject has been selected for treatment on the basis of the methods of the invention.

Once again, corresponding methods are envisaged for WRN and colorectal cancer, BRCA1 and breast cancer, NDRG4 and colorectal cancer and PTEN and cancers such as thyroid carcinomas, melanoma, Leukaemia and gynaecological cancers such as cervical and ovarian cancers.

For all of the relevant methods (pharmacogenetic methods, treatment regimen methods and methods of treatment) of the invention, the DNA demethylating agent may be any agent capable of up regulating transcription of the appropriate gene. A preferred DNA demethylating agent comprises, consists essentially of or consists of a DNA methyltransferase inhibitor. The DNA methyltransferase inhibitor may be any suitable inhibitor of DNA methyltransferase which is suitable for treating cancer in the presence of methylation of the relevant gene. The link between gene methylation and a respective cancer type is known for these genes and so preventing this methylation is predicted to help to treat cancer.

The DNA methyltransferase inhibitor may, in one embodiment, be one which reduces expression of DNMT genes, such as suitable antisense molecules, or siRNA molecules which mediate RNAi for example. The design of a suitable siRNA molecule is within the capability of the skilled person and suitable molecules can be made to order by commercial entities (such as Ambion). Preferably, the DNA methyltransferase gene is (human) DNMTI.

Alternatively, the agent may be a direct inhibitor of DNMTs. Examples include modified nucleotides such as phosphorothioate modified oligonucleotides (see FIG. 6 of Villar-Garea, A. And Esteller, M. DNA demethylating agents and chromatin-remodelling drugs: which, how and why? Current Drug Metabolism, 2003, 4, 11-31) and nucleosides and nucleotides such as cytidine analogues. Suitable examples of cytidine analogues include 5-azacytidine, 5-aza- 2'-deoxycytidine, 5-fluouro-2'-deoxycytidine, pseudoisocytidine, 5,6-dihydro-5-azacytidine, 1-β-D-arabinofuranosyl-5-azacytosine (known as fazabarine) (see FIG. 4 of Villar-Garea, A. And Esteller, M. DNA demethylating agents and chromatin-remodelling drugs: which, how and why? Current Drug Metabolism, 2003, 4, 11-31).

In another embodiment, the DNA methyltransferase inhibitor comprises Decitabine. Full details of this drug can be found at www.supergen.com for example.

Additional DNMT inhibitors include S-Adenosyl-Methionine (SAM) related compounds like ethyl group donors such as L-ethionine and non-alkylating agents such as S-adenosyl-homocysteine (SAH), sinefungin, (S)-6-methyl-6-deaminosine fungin, 6-deaminosinefungin, N4-adenosyl-N4-methyl-2,4-diaminobutanoic acid, 5'-methylthio-5'-deoxyadenosine (MTA) and 5'-amino-5'-deoxyadenosine (Villar-Garea, A. And Esteller, M. DNA demethylating agents and chromatin-remodelling drugs: which, how and why? Current Drug Metabolism, 2003, 4, 11-31).

Further agents which may alter DNA methylation and which may, therefore, be useful in the present compositions include organohalogenated compounds such as chloroform etc, procianamide, intercalating agents such as mitomycin C, 4-aminobiphenyl etc, inorganic salts of arsenic and selenium and antibiotics such as kanamycin, hygromycin and cefotaxim (Villar-Garea, A. And Esteller, M. DNA demethylating agents and chromatin-remodelling drugs: which, how and why? Current Drug Metabolism, 2003, 4, 11-31).

Particulary preferred DNMT inhibitors in the present invention comprise, consists essentially of or consists of 5-azacytidine and/or zebulaine.

The histone deacetylase (HDAC) inhibitor may comprise at least one of trichostatin A (TSA), suberoyl hydroxamic acid (SBHA), 6-(3-chlorophenylureido)caproic hydroxamic acid (3-Cl-UCHA), m-carboxycinnamic acid bishydroxylamide (CBHA), suberoylanilide hydroxamic acid (SAHA), azelaic bishydroxamic acid (ABHA), pyroxamide, scriptaid, aromatic sulfonamides bearing a hydroxamic acid group, oxamflatin, trapoxin, cyclic-hydroxamic-acid containing peptides, FR901228, MS-275, MGCD0103, short-chain fatty acids and N-acetyldinaline.

The invention will now be described with respect to the following non-limiting examples:

DETAILED DESCRIPTION OF THE INVENTION

EXAMPLE 1

Figure 1:
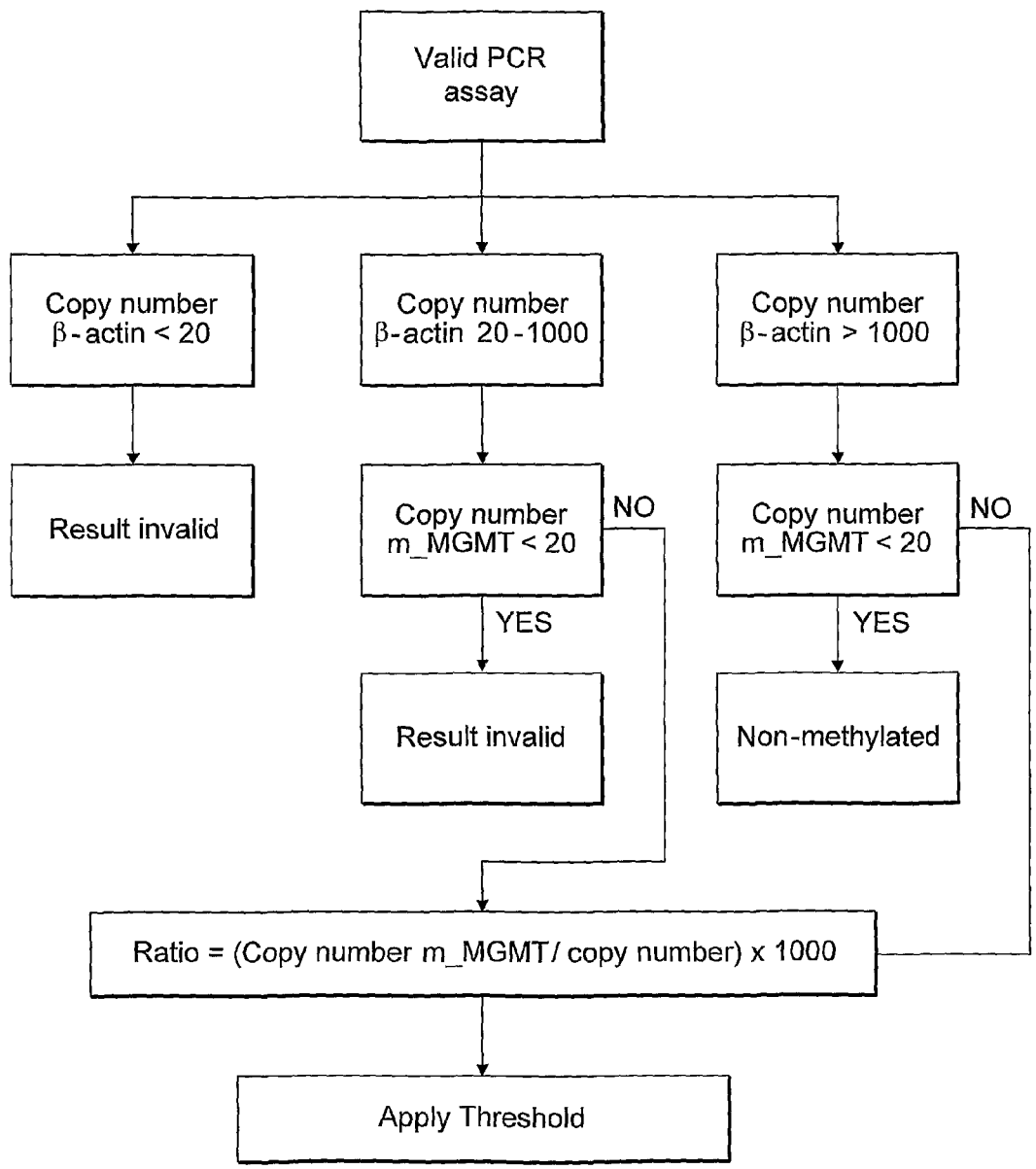
FIG. 1: Decision tree for determination of the MGMT methylation status in clinical samples (real-time MSP).

Correlation Between Testing MGMT Gene Promoter Methylation Status of Glioblastoma Tissue Using Nested Gel-Based and Direct Real-Time Fluorescence-Based Methylation Specific PCR List of Abbreviations:
  Ct values: cycles at which the amplification curves cross the threshold value, as set automatically by the software
  MGMT: $O^6$-methylguanine-DNA methyltransferase
  ACBT: β-actin
  m_MGMT: methylated version of MGMT gene promoter
  u_MGMT: unmethylated version of MGMT gene promoter
  NTC: no-template control
  MSP: Methylation-Specific PCR
  ONCO: OncoMethylome Sciences
  FDA: US Food and Drug Administration
  RTOG: Radiation Therapy Oncology Group
  EORTC: European Organization for Research and Treatment of Cancer
  FFPE: formalin fixed paraffin embedded
  HE stain: Hematoxylin-Eosin stain
  CHUV: Centre Hospitalier Universitaire Vaudois
  ROC: Receiver Operating Characteristic
  AUC: Area Under the ROC Curve
  TMZ: temozolomide
Material and Methods:
Samples and Assays:
  One hundred thirty-four FFPE glioma tissues, predominantly glioblastoma, were obtained from patients who had given their informed consent. Patients were enrolled in clinical trials coordinated at the University Hospitals in Lausanne (Switzerland), Rotterdam (The Netherlands), and Regensburg (Germany). The correlations of the MGMT status with survival will be part of the publications reporting the respective trials (Stupp et al.; van den Bent et al.; Hau et al.; manuscripts in preparation). Of these, 125 were tested once by the CHUV (gel-based MSP), 29 were tested once by ONCO (real-time MSP), and 105 were tested in duplicate by ONCO (real-time MSP). See Table 1 for further details.

TABLE 1

Summary of the samples evaluated by both assays

| Site | Samples | Duplicate test | Single test | Total tests | Valid tests [%] |
|------|---------|----------------|-------------|-------------|-----------------|
| ONCO | 134 | 105 (210 tests) | 29 | 239 | 225/239 [94.2%] |
| CHUV | 125 | 0 | 125 | 125 | 94/125 [75.2%] |

Sample Preparation:

For each tumor sample eight 5 μm consecutive sections were prepared on glass slides. An additional slide stained with Hematoxylin-Eosin (HE) was used to define the tumor area that was subsequently marked on the unstained serial sections. Only tissue comprising sufficient compact and viable tumor tissue was considered, excluding necrotic areas. For samples with a tumor area of less than 0.5×1.0 cm the number of sections was increased accordingly. The prepared sample sections were then divided between the two sites and processed in parallel at ONCO (real-time MSP) and the CHUV (gel-based MSP), according to each laboratory's respective protocols. The laboratories were blinded to the results obtained in the other assay.

Nested-MSP Approach with Visualization of Results on Agarose Gels:

This assay was conducted as published previously (9). In brief, DNA was isolated from the tumor tissue after macro dissection and scraping from the marked slides using the Ex-Wax DNA extraction Kit (S4530, Chemicon) limiting the proteinase digestion to six hours. After the bisulphite treatment step, purified DNA was subjected to MSP using a two step approach with nested primers (19). The first round of PCR amplifies both the methylated as well as the unmethylated version of the MGMT sequence (m_MGMT and u_MGMT). The resulting PCR product of 289 bp served as a template for the second, methylation-specific PCRs, amplifying either m_MGMT or u_MGMT, yielding PCR products of 81 and 93 bp, respectively (7). The specific primers for m_MGMT recognize the fully methylated sequence. The u_MGMT assay served as a control for the PCR. The first PCR consisted of 35 cycles. Two μl of the first PCR was diluted 1/20 and input to the second PCR of 30 cycles. The products from the second PCR were visualized on 4% agarose gels (NuSieve 3:1) to determine the MGMT methylation status. The outcome of the nested gel-based MSP was considered valid when the following four criteria were fulfilled: a) PCR products of the expected sizes were detected on agarose gel (single bands); b) either a band for u_MGMT, m_MGMT, or both was present; c) routinely included positive and negative controls, including a no-template control (NTC) gave the expected result, and d) the result was confirmed in an independent experiment starting with the bisulphite treatment of DNA. The valid results of all clinical samples were classified as methylated or non-methylated depending on the presence or absence of a band for m_MGMT. This procedure was used for the analysis of all samples in the laboratory in the CHUV.

Real-Time MSP

DNA Isolation:

Slide sets of slices of FFPE tumor were tested using the real-time MSP assay. Of 134 samples, 29 were tested once. For 105 of the samples, the isolated DNA was split in two equal portions and the two portions were processed independently beginning at the bisulphite conversion step (Table 1).

Macro-dissected FFPE tissue as marked on the slides was de-paraffinized in 750 μl xylene for 2 h. Then, 250 μl of 70% ethanol was added before centrifugation at 13000 rpm for 15 min. The supernatant was removed and the samples were air dried for 20 min at room temperature. DNA was extracted using the classical phenol/chloroform extraction method and resuspended in 50 μl LoTe (3 mM TRIS, 0.2 mM EDTA, pH 8.0). The DNA was quantified using the Picogreen® dsDNA quantitation kit (Molecular Probes, Invitrogen) following manufacturer's recommendations. A DNA provided with the kit was used to prepare a standard curve (from 1 to 800 ng/ml). The data were collected using a FluoStar Galaxy plate reader (BMG Lab technologies, Germany).

DNA Modification:

Up to 1.5 μg of DNA from each sample was modified using sodium bisulphite. This reaction selectively deaminates unmethylated Cytosine residues resulting in a conversion to Uracil, while 5-methyl Cytosine residues are not modified. The bisulphite reaction was performed using the EZ DNA Modification Kit™ (Zymo, D5002) according to the manufacturer's recommendation, which includes successive steps of conversion, desalting and desulfonation. At the end of the procedure, the modified DNA was eluted in 25 μl of 1 mM TRIS-HCL pH 8.0, and then stored at −80° C.

Preparation of Standards:

Plasmid DNA was prepared by cloning of the relevant sequences into TOPO® TA vectors (TOPO® cloning kit, Invitrogen®). m_MGMT was obtained from the methylated sequence present in the SW48 cell line. After isolating the plasmids from the bacteria using the QIAprep® spin midiprep kit (Qiagen GmbH; according to the manufacturer's protocol), sequences were confirmed by MWG Biotech, Germany (data not shown). The plasmids were then linearized by digestion with the restriction enzyme BamHI (Roche). The linearized plasmid was purified using the QIAquick® PCR purification kit (Qiagen GmbH; according to the manufacturer's protocol). The plasmid concentration was determined by $OD_{260}$ measurement. A stock solution of $2 \times 10^7$ copies/5 μl ($4 \times 10^6$ copies/μl) was prepared and stored at −80° C. until use. Dilutions of standard curves ($2 \times 10^6$-$2 \times 10^1$ copies/5 μl) for m_MGMT and ACTB were freshly prepared for each experiment.

Real-Time PCR:

The analyte (m_MGMT and ACTB) quantifications were performed by real-time PCR assays. These consisted of parallel amplification/quantification processes using specific primer and primer/detector pairs for each analyte using the Amplifluor® assay format on an ABI Prism® 7900HT instrument (Applied Biosystems). The analyte defined in the real-time PCR was the MGMT promoter sequence and detects the fully methylated version. ACTB was used as a reference gene in the assay. The Amplifluor® forward primers are preceded by the detection elements (underlined). The amplicon size is 136 bp for the m_MGMT analyte, and 125 bp for the ACTB analyte. These amplicons include the Amplifluor detection sequence. Sequence details for both forward and reverse primers are as follows:

```
Forward Primer MGMT:
                    (SEQ ID NO: 1 plus SEQ ID No: 2)
5'-agcgatgcgttcgagcatcgcutttcgacgttcgtaggttttcg
c-3'

Reverse Primer MGMT:
                                   (SEQ ID NO: 3)
5'-ctcgaaactaccaccgtcccga-3'
```

```
Forward Primer beta-actin:
                    (SEQ ID NO: 1 plus SEQ ID NO: 4)
5'-agcgatgcgttcgagcatcgcutagggagtatataggttgggga
agtt-3'

Reverse Primer beta-actin:
                                       (SEQ ID NO: 5)
5'-aacacacaataacaaacacaaattcac-3'
```

The MGMT target sequence is located on chromosome 10 between positions 131155505 and 131155619, while the ACTB target sequence is located on chromosome 7 between positions 5538428 and 5538325, based on version 36.1 of the NCBI human genome.

The final primer concentrations in the reaction mix were 100 nM for both forward primer/detector and reverse primer. 12.5 μl of iTaq™ Supermix with Rox (BioRad, 2× buffer) were used per PCR reaction. The total volume per reaction, including 5 μl of modified template DNA, was 25 μl. The ABI 7900HT SDS instrument was started 10 min before use, allowing the heated cover to reach 105° C. The following thermal profile was used: Stage1: 50° C. for 2 min, Stage2: 95° C. for 10 min, Stage3: 95° C. for 15 sec, 62° C. for 1 min (=plateau-data collection) for 45 repeats.

Quantification:

To quantify the results of the real-time MSP assay, two standard curves were produced, one for the reference gene (ACTB) and one for the methylated version of the MGMT gene using the standards described above. The results were generated using the SDS 2.2 software (Applied Biosystems), exported as Ct values (cycle number at which the amplification curves cross the threshold value, set automatically by the software), and then used to calculate copy numbers based on a linear regression of the standard curve values. One hundred-five clinical samples were measured in duplicate. Lysates of cell lines SW48 DNA and HT29 were included in each experiment as positive and negative controls, respectively, and entered the procedure at the DNA extraction step.

The results of a run were considered valid when the following five criteria were met: a) slopes of both standard curves above −4 (PCR efficiency>77.8%); b) $R^2$ of at least relevant data points above 0.990; c) routinely included NTC not amplified; d) 10% of a 1 μg conversion reaction of the positive cell line assay control SW48 was detectable; and e) 10% of a 1 μg conversion reaction of the negative cell line assay control HT29 was not detected within the standard curve.

Normalization of Results:

To compensate for variations due to differences in sample volume and preparation, the m_MGMT copy numbers derived were divided by the ACTS copy numbers for that sample. This figure was multiplied by 1000 for convenient handling, and the result referred to as the ratio value.

Statistics

Statistical analyses were carried out with R, a free software environment.

Dichotomization of the Real-Time MSP Results:

The ratio values were $\log_2$ transformed. The evaluation of the distribution of the m_MGMT measurements in the density plot was performed using 99 duplicate samples (see Table 2 for more details). Gaussian mixture models were fitted to the average data $\log_2(1000*m\_MGMT/ACTB)$ of the real-time MSP duplicates (20-22).

One sample showed a high discordance between the duplicate tests. Repeat testing of the sample produced consistent results, but this sample was excluded from the curve fitting exercise, which thus included 98 samples.

Results

FFPE glioma tissues were analyzed in parallel to determine the methylation status of the MGMT promoter in independent laboratories using two distinct technical approaches. This blinded study compared the results obtained by a real-time MSP on a high throughput platform to the gel-based MSP assay previously shown to predict benefit from the addition of the alkylating agent temozolomide to the treatment of newly diagnosed glioblastoma in two clinical trials (8, 9).

Validity of Results

The assays were compared by evaluating 134 FFPE glioma samples by real-time MSP (29 single and 105 duplicate tests) and 125 FFPE glioma samples by gel-based MSP (all single tests as defined in references 2 and 3). The real-time MSP assay produced valid results in 94.2% versus 75.2% of valid tests for the gel-based assay (Table 1). Among the duplicate real-time MSP tests 5 of 6 invalid results were duplicated. The validity rates are based on the respective validation criteria for each assay (for gel-based MSP see references 2 and 3, for real-time MSP see FIG. 1).

Definition of Cut-Off for m_MGMT Status

Figure 3:
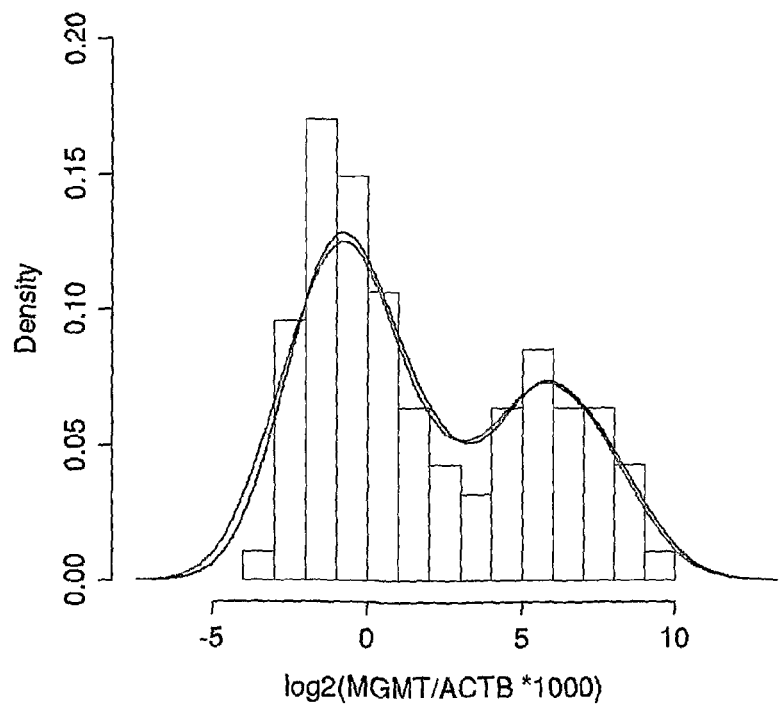
FIG. 3: Density plot of normalized m_MGMT copy number in glioblastoma. Histogram of average results from 99 samples with duplicate measurements, the respective lines represent results from each replicate. Only samples with Ct values <40 for m_MGMT are included. The minimum between the two Gaussian curves is at the ratio of 3 $\log_2$ (m_MGMT/ACTB*1000).
Figure 4A:
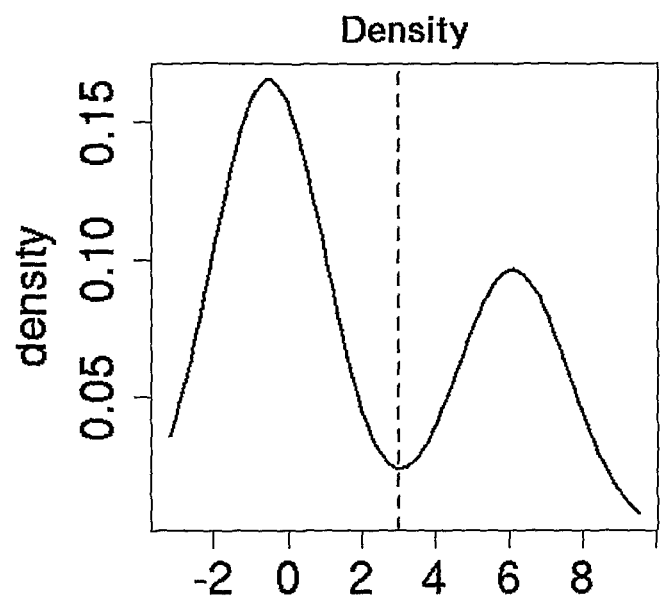
FIG. 4: Definition of natural cut-off for m_MGMT. Density (A), Classification (B), Uncertainty (C) of observations belonging to classes and posterior Probability (D) to be in class 2 (m_MGMT) from a fitted mixture model applied to the average $\log_2$(m_MGMT/ACTB*1000). In the classification plot (B), all of the data are displayed at the bottom, with the separated classes shown at different levels above. The dashed line represents the optimal cut-off according to the selected model (3 in $\log_2$ units, or ratio of 8). The area between the grey dotted lines (D) defines a possible grey zone; the threshold for 95% probability of non-m_MGMT is 2 in $\log_2$ space (ratio of 4), and of 4 in $\log_2$ space (ratio of 16) for m_MGMT, respectively.
Figure 4B:
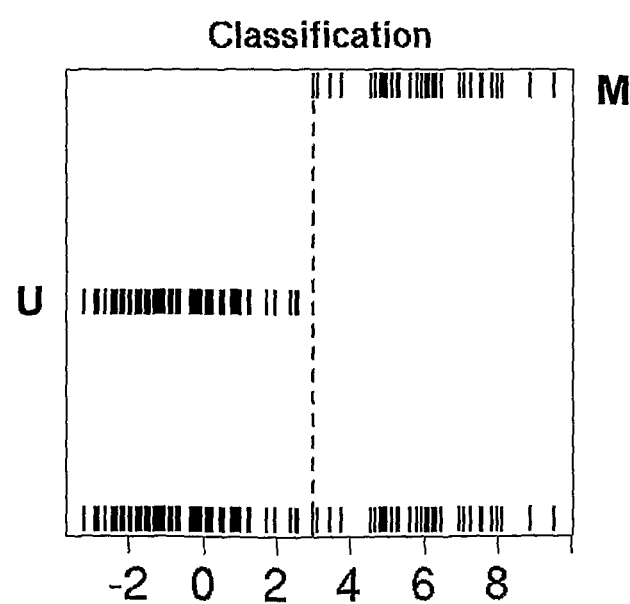
Figure 4C:
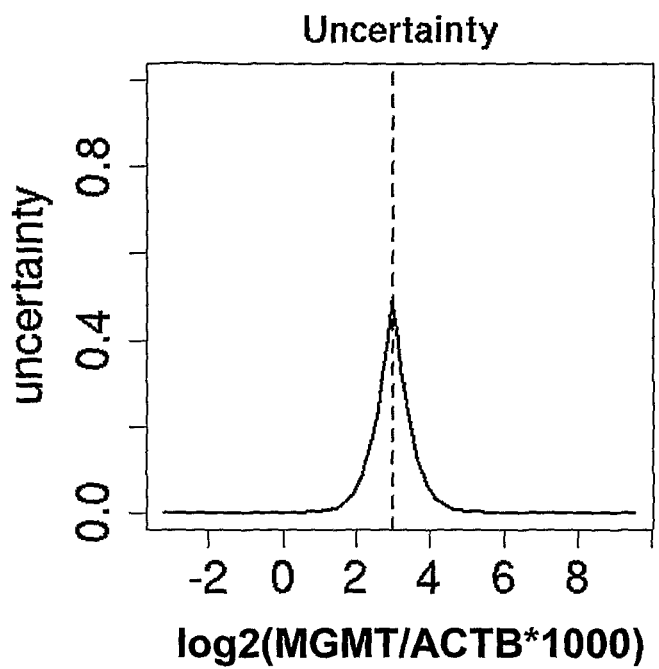
Figure 4D:
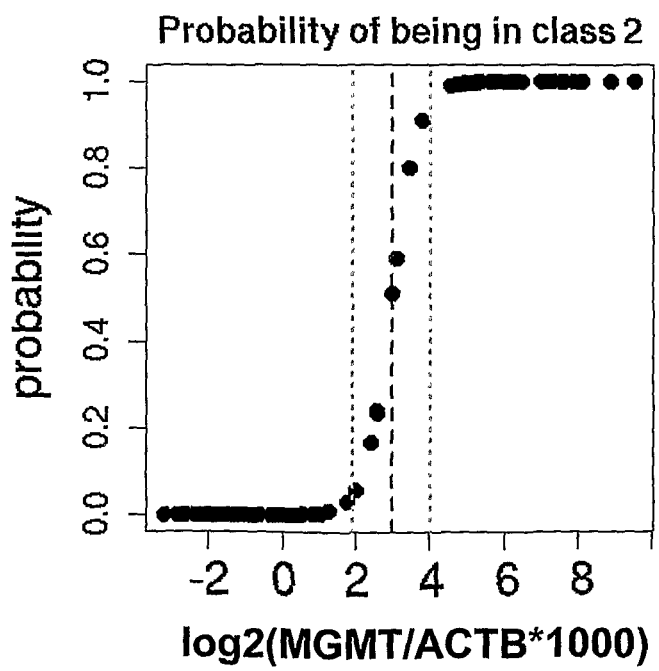

Samples evaluated in duplicate by the newly established real-time MSP assay revealed a clear bimodal distribution of the measurements as shown in FIG. 3. This allows definition of a discriminatory cut-off for the determination of the MGMT methylation status by fitting a normal mixture model. The best model based on 99 samples yields 2 Gaussians of equal variance ($\sigma^2=2.3$), and of a $\log_2$ ratio mean of −0.52 and 6.1, respectively (FIG. 4A). This corresponds to a mean ratio value [1000*m_MGMT/ACTB] of 0.7 and 68.1, respectively. According to this model which defines 2 classes, non-m_MGMT and m_MGMT, the cut-off corresponds to a $\log_2$ ratio value of 3 (FIG. 4B). Close to this cut-off there are some samples for which the probability of belonging to one class or the other is close to 50% and as a direct consequence the uncertainty of the classification is very high (FIG. 4C). This suggests the use of a grey zone for diagnostic purposes, and allows definition of different thresholds depending on the clinical questions asked. The threshold for 95% probability of methylation is a $\log_2$ ratio value of 4, and 2 for non-m_MGMT (FIG. 4D).

Reproducibility of the Real-Time MSP Assay

Figure 2:
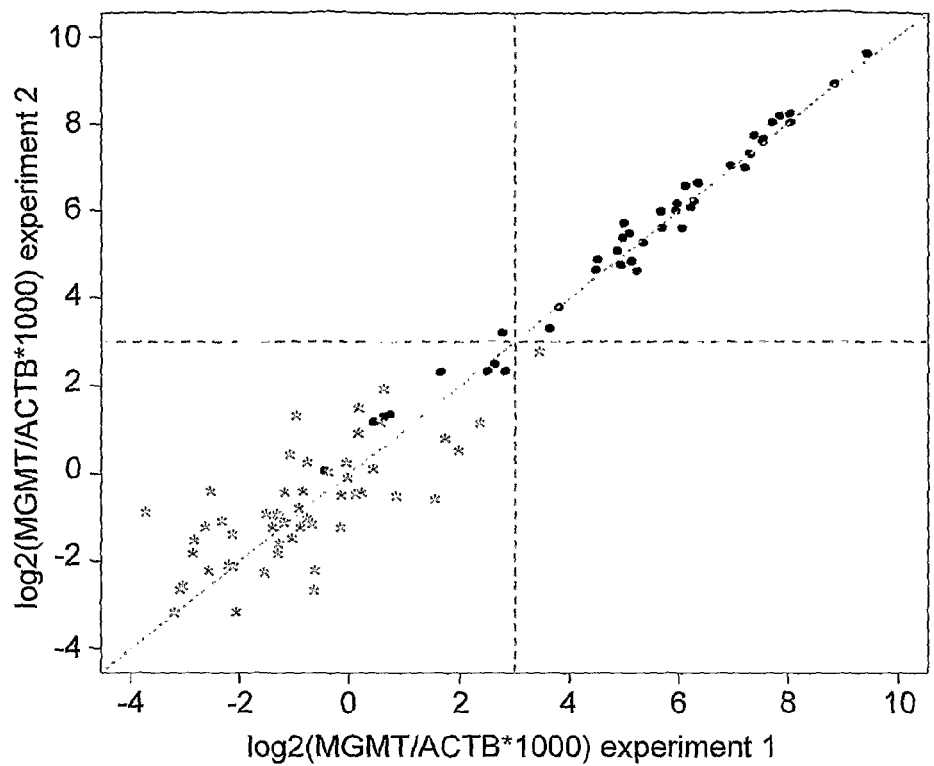
FIG. 2: Reproducibility of real-time MSP duplicate measurements. Dotted line represents identity line (x=y), and dashed lines represent the cut-off between m_MGMT and non-m_MGMT samples according to Gaussian mixture model as defined. Pearson correlation 0.996, Spearman correlation 0.93, N=99. Black dots represent samples with m_MGMT copies >20; Grey star represent samples with less than 20 m_MGMT copies but with a m_MGMT Ct value <40.

Ninety nine of the 105 duplicate samples yielded a valid result for both real-time MSP replicates (FIG. 2). Many of the samples with very low $\log_2$ ratio-values show m_MGMT copy numbers below the lower limit of the standard curve (the lower limit of the standard curve is 20 copies). In practice, no ratio is calculated for these samples, and they are considered non-methylated. This reproducibility shows that the efficacy of the bisulphite treatment of the DNA introduced no major variability into the assay.

Figure 5:
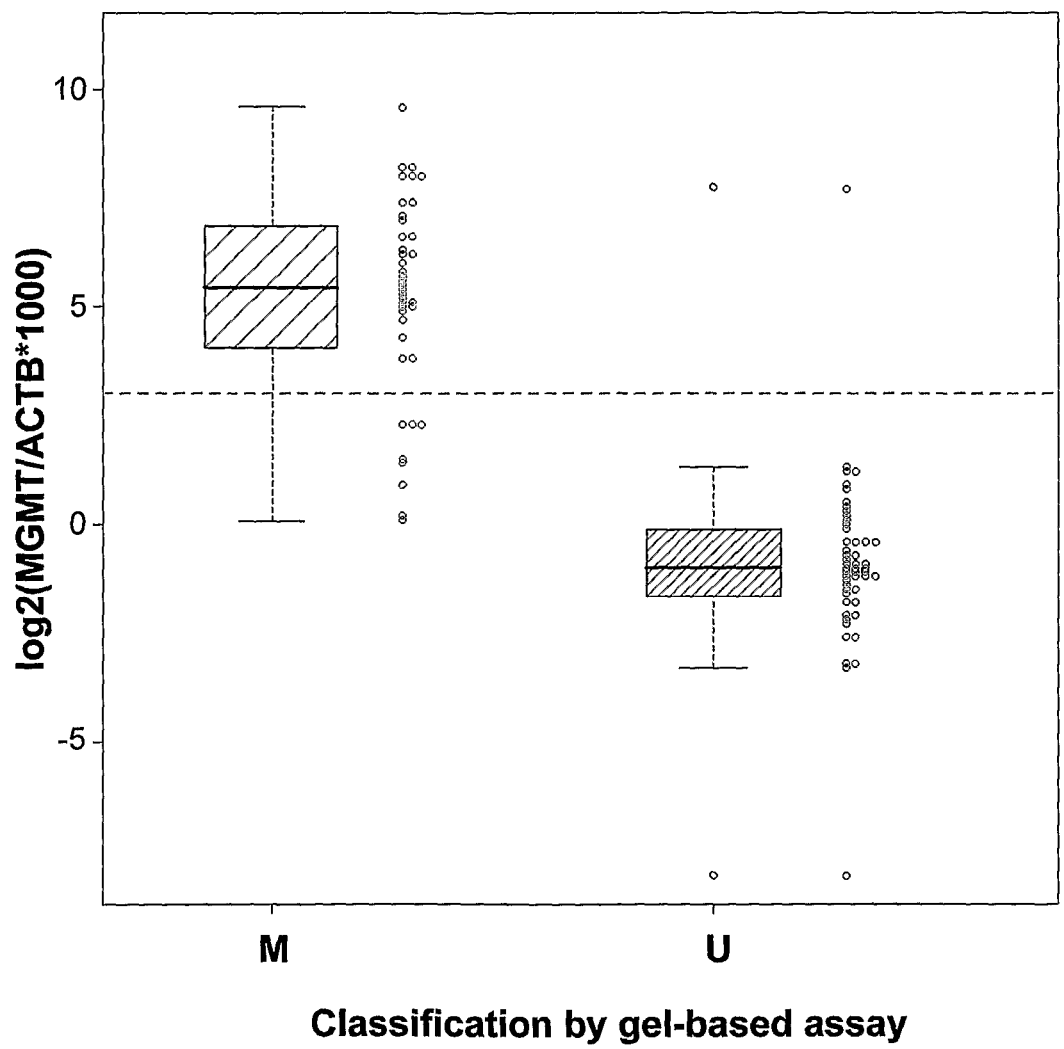
FIG. 5. Comparison between direct real-time MSP and nested, gel-based MSP results. Boxplots and stripcharts of the $\log_2$(m_MGMT/ACTB*1000) (y-axis) of the results determined for 91 samples by direct real-time MSP assay are compared to the respective classification by the nested, gel-based assay into non-m_MGMT (U) and m_MGMT (M) samples (x-axis). Dashed lines represent the cut-off between m_MGMT and non-m_MGMT samples according to Gaussian mixture model.

Concordance Between Real-Time and Gel-Based MSP Assays:

The methylation status of ninety one samples with a valid result for both real-time and gel-based MSP assays is shown in Table 2. There is a good concordance between the two tests (82/91 samples [90%]). FIG. 5 shows that there is a good separation between the real-time MSP values for methylated and non methylated samples. Cohen's Kappa coefficient using a cut-off at the $\log_2$ ratio-value of 3, was 0.80 (95% CI: 0.67-0.92), similarly reflected in the one sample proportions test (with continuity correction) with agreement of 0.90 (95% CI: 0.82-0.95).

TABLE 2

Concordance between ONCO and CHUV results (m_MGMT and non-m_MGMT measurements)

|  |  | ONCO | | |
|---|---|---|---|---|
|  |  | m_MGMT | non-m_MGMT | Total |
| CHUV | m_MGMT | 32 | 1 | 33 |
|  | non-m_MGMT | 8 | 50 | 58 |
|  | Total | 40 | 51 | 91 |

Discussion:

A sensitive and specific real-time MSP assay has been developed to reliably detect the methylation status of the MGMT gene promoter in clinical samples of FFPE tissues for diagnostic purposes. The methylation status result of this test is in good concordance with results obtained with the gel-based MSP assay that established the predictive value of the MGMT methylation status in glioblastoma for benefit from temozolomide therapy (9).

Although normalization provides a more reproducible assay, it may contribute to the few discrepants seen in this study, as they are mostly samples with detectable levels of m_MGMT but also high levels of ACTB. Some discordance is not surprising, since the cut-off of the gel-based MSP assay is defined by visual presence or absence of the PCR product without normalization. Normalization to DNA content, measured here as ratio to ACTS, is not an absolute measurement, since "normal tissue" contaminations are present in all clinical tumor samples, and genomic copy number aberrations are common in glioblastoma, including on chromosomes 10 and 7, where the MGMT and ACTB gene reside, respectively. However, neither homozygous deletions nor high level amplifications have been reported for MGMT or ACTB that potentially could be problematic for interpretation of results. The ACTS is also used as a control gene by other groups using real-time PCR for quantitative DNA methylation analysis (17).

The real-time MSP assay more often yielded a valid result with FFPE tissue specimens than the gel-based MSP assay. This improved performance is likely due to the smaller amplicon size of the real-time assay that is more appropriate for FFPE samples known to yield limited DNA quality.

The quantitative measure obtained and the bimodal distribution of the values will allow definition of clinically relevant thresholds for stratified therapy. Initial cut-offs, in use today, were determined from limited correlation studies with the gel based MSP assay. This study extends that correlation, confirms the initial ratio cut-offs used and demonstrates that there is an important separation of values around that cut-off, suggesting that there are two distinct populations underlying the data, and that few samples would be expected with values near the cut-off. To arrive at the best, most clinically useful cut off for patient management, results relating the real-time MSP assay to patient response must be studied.

The test described here is being prospectively used for randomizing patients in an ongoing clinical phase III trial (RTOG 0525/EORTC 26052-22053) testing standard versus dose-intense adjuvant TMZ in patients with newly diagnosed glioblastoma (trial is reviewed in Stupp et al. (11)). Among the goals of this trial is to prospectively validate the use of MGMT methylation status for predicting benefit from alkylating agent therapy and it will provide further information on a clinically relevant cut-off for m_MGMT.

This sensitive and robust high through-put test for evaluating the methylation status of the MGMT gene may provide an important pharmacogenomic tool for individualized management of patients considered for treatment with temozolomide or other alkylating agent chemotherapy.

REFERENCES

1. Pegg A E. Repair of O(6)-alkylguanine by alkyltransferases. Mutat Res 2000; 462:83-100.
2. Gerson S L. MGMT: its role in cancer aetiology and cancer therapeutics. Nat Rev Cancer 2004; 4:296-307.
3. Stojic L, Cejka P, Jiricny J. High doses of SN1 type methylating agents activate DNA damage signaling cascades that are largely independent of mismatch repair. Cell Cycle 2005; 4:473-7. Epub 2005 Mar. 10.
4. Qian X C, Brent T P. Methylation hot spots in the 5' flanking region denote silencing of the O6-methylguanine-DNA methyltransferase gene. Cancer Res 1997; 57:3672-7.
5. Watts G S, Pieper R O, Costello J F, Peng Y M, Dalton W S, Futscher B W. Methylation of discrete regions of the O6-methylguanine DNA methyltransferase (MGMT) CpG island is associated with heterochromatinization of the MGMT transcription start site and silencing of the gene. Mol Cell Biol 1997; 17:5612-9.
6. Esteller M, Hamilton S R, Burger P C, Baylin S B, Herman J G. Inactivation of the DNA repair gene O6-methylguanine-DNA methyltransferase by promoter hypermethylation is a common event in primary human neoplasia. Cancer Res 1999; 59:793-7.
7. Esteller M, Garcia-Foncillas J, Andion E, Goodman S N, Hidalgo O F, Vanaclocha V, et al. Inactivation of the DNA-repair gene MGMT and the clinical response of gliomas to alkylating agents. N Engl J Med 2000; 343:1350-4.
8. Hegi M E, Diserens A C, Godard S, Dietrich P Y, Regli L, Ostermann S, et al. Clinical trial substantiates the predictive value of O-6-methylguanine-DNA methyltransferase promoter methylation in glioblastoma patients treated with temozolomide. Clin Cancer Res 2004; 10:1871-4.
9. Hegi M E, Diserens A C, Gorlia T, Hamou M F, de Tribolet N, Weller M, et al. MGMT gene silencing and benefit from temozolomide in glioblastoma. New Engl J Med 2005; 352:997-1003.
10. Stupp R, Mason W P, van den Bent M J, Weller M, Fisher B, Taphoorn M J B, et al. Radiotherapy plus concomitant and adjuvant temozolomide for glioblastoma. N Engl J Med 2005; 352:987-96.
11. Stupp R, Hegi M E, van den Bent M J, Mason W P, Weller M, Mirimanoff R O, Cairncross J G. Changing paradigms—an update on the multidisciplinary management of malignant glioma. Oncologist 2006; 11:165-80.
12. Everhard S, Kaloshi G, Criniere E, Benouaich-Amiel A, Lejeune J, Marie Y, et al. MGMT methylation: a marker of response to temozolomide in low-grade gliomas. Ann Neurol 2006; 60:740-3.
13. Brandes A A, Tosoni A, Cavallo G, Reni M, Franceschi E, Bonaldi L, et al. Correlations between O6-methylguanine DNA methyltransferase promoter methylation status, 1p and 19q deletions, and response to temozolomide in anaplastic and recurrent oligodendroglioma: a prospective GICNO study. J Clin Oncol 2006; 24:4746-53.
14. Esteller M, Corn P G, Baylin S B, Herman J G. A gene hypermethylation profile of human cancer. Cancer Res 2001; 61:3225-9.
15. Criniere E, Kaloshi G, Laigle-Donadey F, Lejeune J, Auger N, Benouaich-Amiel A, et al. MGMT prognostic impact on glioblastoma is dependent on therapeutic modalities. J Neurooncol 2007; 83:173-9.
16. Laird P W. The power and the promise of DNA methylation markers. Nat Rev Cancer 2003; 3:253-66.
17. Eads C A, Danenberg K D, Kawakami K, Saltz L B, Blake C, Shibata D, et al. MethyLight: a high-throughput assay to measure DNA methylation. Nucleic Acids Res 2000; 28:E32.
18. Mikeska T, Bock C, El-Maarri O, Hubner A, Ehrentraut D, Schramm J, et al. Optimization of Quantitative MGMT Promoter Methylation Analysis Using Pyrosequencing and Combined Bisulfite Restriction Analysis. J Mol Diagn 2007.
19. Palmisano W A, Divine K K, Saccomanno G, Gilliland F D, Baylin S B, Herman J G, Belinsky S A. Predicting lung cancer by detecting aberrant promoter methylation in sputum. Cancer Res 2000; 60:5954-8.
20. Fraley C, Raftery A E. Model-Based Clustering, Discriminant Analysis, and Density Estimation. J American Statistical Assoc 2002; 97:611-31.
21. Fraley C, Raftery A E. MCLUST Version 3 for R: Normal Mixture Modeling and Model-based Clustering. Vol. Washington: Department of Statistics, University of Washington, 2006.
22. Altman D G. Practical Statistics for Medical Research. London: Chapman & Hall, 1991.
23. Ogino S, Kawasaki T, Brahmandam M, Cantor M, Kirkner G J, Spiegelman D, et al. Precision and performance characteristics of bisulfite conversion and real-time PCR (MethyLight) for quantitative DNA methylation analysis. J Mol Diagn 2006; 8:209-17.
24. Califice S, et al Poster 2005 "O6-Alkylguanine-DNA Alkyltransferase Meeting", Keele, UK, 06-09/08/2005
25. Esteller M, Gaidano G, Goodman S N, Zagonel V, Capello D, Botto B, Rossi D, Gloghini A, Vitolo U, Carbone A, Baylin S B, Herman J G. Hypermethylation of the DNA repair gene O(6)-methylguanine DNA methyltransferase and survival of patients with diffuse large B-cell lymphoma. J Natl Cancer Inst. 2002 Jan. 2; 94(1):26-32.
26. Sperry, et al. The emerging roles of DNA methylation in the clinical management of prostate cancer. Endocrine-Related Cancer (2006) 13 357-377
27. Zitt et al. DNA methylation in colorectal cancer—Impact on screening and therapy monitoring modalities? Disease Markers 23 (2007) 51-71

EXAMPLE 2

Amplifluor Experiments: Testing Different Primer Sequences and Reading Temperatures Amplifluor is a primer-based methodology. It lacks the third oligo nucleotide "probe" that typifies TaqMan and Molecular Beacon technologies. Without this third layer of specificity, amplifluor primers can fluoresce in response to non-specific amplification such as primer-dimers. Therefore it is important to carefully select primer sequences to overcome this behavior.

Initial Results

Initial MGMT amplifluor results were obtained using the primer set shown in Table 3. The final primer concentrations in the Amplifluor reaction mix were 100 nM for both forward primer/detector and reverse primer. 12.5 µl of iTaq™ Supermix with Rox (BioRad, 2× buffer) were used per PCR reaction. The total volume per reaction, including 5 µl of no-template control (NTC: water control with no DNA present), was 25 µl. The following thermal profile was used on the ABI 7900 HT SDS instrument: Stage1: 50° C. for 2 min, Stage2: 95° C. for 10 min, Stage3: 95° C. for 15 sec, 62° C. for 1 min (=plateau-data collection) for 45 repeats.

The amplifluor assay resulted in positive NTCs due to primer-dimer formation: 8 potential dimer residues were identified in this set of primers.

TABLE 3 primer details initial MGMT amplifluor design

| Name | Details | Sequence |
|------|---------|----------|
| 344 | MGMT forward detector | 5'-AGCGATGCGTTCGAGCATCGCUTTTCGACGTT CGTAGGTTTTCGC-3' amplifluor detector moiety MGMT forward primer sequence (SEQ ID NO: 1 plus SEQ ID NO: 2) |
| PMR91 | MGMT reverse primer | 5'-GCACTCTTCCGAAAACGAAACG-3' (SEQ ID NO: 7) |

Table 4 gives an overview of the positive Ct values observed for 12 NTC samples tested through the initial MGMT amplifluor assay.

TABLE 4

NTC performance initial MGMT amplifluor design

| Sample | Task | Ct PMR91 |
|--------|------|----------|
| 1 | NTC | 37.38 |
| 2 | NTC | 36.78 |
| 3 | NTC | 36.67 |
| 4 | NTC | 37.15 |
| 5 | NTC | 36.69 |
| 6 | NTC | 36.59 |
| 7 | NTC | 37.17 |
| 8 | NTC | 36.32 |
| 9 | NTC | 37.71 |
| 10 | NTC | 36.71 |
| 11 | NTC | 37.86 |
| 12 | NTC | 36.65 |

New Primer Designs

To overcome the problem of positive NTCs, 6 different reverse primer sequences (see Table 5) were designed and 14 NTC samples were tested in parallel through all new designed assays. The forward primer/detector sequence remained unchanged. The same PCR conditions were used as set out above.

TABLE 5

Newly designed reverse primer sequences

| Primer name | Reverse primer sequence |
|-------------|--------------------------|
| PMR103 (SEQ ID NO: 8) | 5'-TAAAAACGCCTACAAAACCACTCG-3' |
| PMR104 (SEQ ID NO: 9) | 5'-AAAAACGCCTACAAAACCACTCGA-3' |
| PMR105 (SEQ ID NO: 3) | 5'-CTCGAAACTACCACCGTCCCGA-3' |
| PMR106 (SEQ ID NO: 10) | 5'-CTCGAAACTACCACCGTCCCG-3' |
| PMR108 (SEQ ID NO: 11) | 5'-ACTCCGCACTCTTCCGAAAACGA-3' |

TABLE 5-continued

Newly designed reverse primer sequences

| Primer name | Reverse primer sequence |
|---|---|
| PMR111 (SEQ ID NO: 12) | 5'-AACTCCGCACTCTTCCGAAAACG-3' |

Table 6 summarizes the Ct values obtained for the 6 new primer designs. A high variation in NTC performance was observed depending on the chosen primer set. The best NTC performance was obtained for PMR105: 13 out of 14 tested water controls resulted in Ct values above 40.

The applied test run validation criteria for the amplifluor assay are defined in such a way that a "valid" Ct value has to be <40 (based on a theoretical definition: if there was one copy in the PCR reaction to be amplified it would take 40 cycles at a PCR efficiency of 100%). Ct values above 40 are considered as 'invalid'. Accordingly, a signal is considered to be negative in real-time MSP when it is classified as "undetermined" or when its Ct value is above 40.

TABLE 6

NTC performance of new MGMT designs

| Sample | Task | Ct PMR103 | Ct PMR104 | Ct PMR105 | Ct PMR106 | Ct PMR108 | Ct PMR111 |
|---|---|---|---|---|---|---|---|
| 1 | NTC | 40.86 | 37.17 | 49.47 | 40.10 | 38.99 | 39.44 |
| 2 | NTC | 41.35 | 35.32 | 40.60 | 39.38 | 39.96 | 37.88 |
| 3 | NTC | 42.46 | 35.51 | 54.59 | 41.53 | 38.54 | 40.56 |
| 4 | NTC | 38.62 | 35.83 | 43.83 | 39.31 | 40.30 | 38.78 |
| 5 | NTC | 38.65 | 35.59 | 40.91 | 38.66 | 38.08 | 38.28 |
| 6 | NTC | 39.07 | 35.34 | 40.49 | 38.05 | 39.29 | 40.43 |
| 7 | NTC | 39.29 | 35.46 | 44.41 | 37.92 | 38.61 | 39.54 |
| 8 | NTC | 34.95 | 37.70 | 41.69 | 37.17 | 38.85 | 39.53 |
| 9 | NTC | 37.61 | 36.42 | 45.74 | 39.04 | 39.65 | 38.73 |
| 10 | NTC | 38.91 | 36.37 | 40.19 | 37.97 | 38.29 | 39.28 |
| 11 | NTC | 39.78 | 37.63 | 37.98 | 40.51 | 39.41 | 39.52 |
| 12 | NTC | 38.80 | 37.09 | 43.22 | 38.23 | 39.30 | 38.74 |
| 13 | NTC | 36.34 | 33.94 | 45.92 | 38.70 | 38.48 | 38.38 |
| 14 | NTC | 40.93 | 36.53 | 40.18 | 42.99 | 38.91 | 39.40 |

Temperature Gradient

PMR105 was retained for further analysis. A temperature gradient was performed to investigate whether higher reading temperatures could improve the NTC performance.

The same reaction mixture and cycling conditions were used as set out above.

5 different reading temperatures were tested on the I-cycler real-time instrument from BioRad: 62° C., 64.1° C., 66° C., 68.6° C. and 70.5° C.

Eight water controls were run per temperature, in addition a serial dilution of cloned MGMT M promoter ($2\times10^6$, $2\times10^4$, $2\times10^2$ and $2\times10^1$ copy numbers) was tested to assess how higher reading temperatures influence the sensitivity and PCR efficiency of the targeted assay. Corresponding results are summarized in Table 7.

TABLE 7

Assay (including MGMT serial dilution and NTC) performance using higher reading temperatures

| | Reading temperatures and PCR efficiency | | | | |
|---|---|---|---|---|---|
| Quantity | 62° C. 96% | 64.1° C. 98% | 66° C. 102% | 68.6° C. 101% | 70.5° C. 93% |
| 2000000 | 17.80 | 17.80 | 17.90 | 18.90 | 27.30 |
| 20000 | 24.80 | 24.80 | 24.70 | 25.50 | 33.80 |

TABLE 7-continued

Assay (including MGMT serial dilution and NTC) performance using higher reading temperatures

| | Reading temperatures and PCR efficiency | | | | |
|---|---|---|---|---|---|
| Quantity | 62° C. 96% | 64.1° C. 98% | 66° C. 102% | 68.6° C. 101% | 70.5° C. 93% |
| 200 | 31.70 | 31.80 | 31.80 | 32.70 | 41.20 |
| 20 | 34.90 | 34.50 | 33.90 | 35.10 | 44.80 |
| 0 (NTC) | 36.20 | 37.80 | 47.50 | 39.60 | 48.80 |
| 0 (NTC) | 36.70 | 37.10 | 36.60 | 43.00 | 51.60 |
| 0 (NTC) | 36.90 | 38.10 | 40.80 | 38.40 | 40.80 |
| 0 (NTC) | 36.90 | 37.50 | 38.20 | 40.00 | 42.40 |
| 0 (NTC) | 38.20 | 37.80 | 37.60 | 37.80 | 41.60 |
| 0 (NTC) | 38.20 | 37.10 | 37.60 | 42.20 | 40.70 |
| 0 (NTC) | 39.30 | 38.60 | 36.70 | 39.70 | 40.70 |
| 0 (NTC) | 45.20 | 37.30 | 37.80 | 43.00 | 39.00 |

Based on Table 7, it can be concluded that higher reading temperatures do improve the NTC performance but at the same time reduces the assay sensitivity.

Reading temperatures 62° C. and 68.6° C. were retained for further analysis. Both temperatures were tested on an initial set of 13 clinical samples to evaluate the sensitivity issue.

Clinical Results 13 glioma samples were run through the MGMT Amplifluor assay (PMR105) testing 2 different reading temperatures: 62° C. and 68.6° C.

Final primer concentrations in the Amplifluor reaction mix were 100 nM for both forward primer/detector and reverse primer. 12.5 µl of iTaq™ Supermix with Rox (BioRad, 2× buffer) were used per PCR reaction. The total volume per reaction, including 5 µl of bisulfite treated DNA, was 25 µl. The following thermal profile was used on the ABI 7900 HT SDS instrument: Stage1: 50° C. for 2 min, Stage2: 95° C. for 10 min, Stage3: 95° C. for 15 sec, 62° C. (alternatively 68.6° C.) for 1 min (=plateau-data collection) for 45 repeats. A serial dilution ($2\times10^6$-20 copies) of MGMT M promoter was included to determine the copy numbers of the unknown samples by interpolation of their Ct values to the standard curve. Results are summarized in Table 8.

TABLE 8

Performance of clinical samples using different reading temperatures

| Sample no | Copies MGMT (PMR105) 62° C. | Copies MGMT (PMR105) 68.6° C. |
|---|---|---|
| 84 | 45 | 1 |
| 253 | 21 | 0 |
| 262 | 330 | 68 |
| 269 | 5 | 0 |
| 284 | 742 | 76 |
| 293 | 3 | 0 |
| 302 | 4 | 0 |
| 309 | 48 | 0 |
| 322 | 4 | 0 |
| 403 | 948 | 262 |
| 433 | 2 | 1 |
| 460 | 277 | 28 |
| 532 | 9 | 0 |

Reading at 68.6° C. results in a considerable loss of sensitivity compared to a reading temperature of 62° C. It can be concluded that best workable results for the MGMT Amplifluor assay are obtained using the reverse primer design PMR105 in combination with a reading temperature of 62° C.

EXAMPLE 3

Additional Genes Tested Through Amplifluor

We developed a direct real-time fluorescence based methylation-specific PCR assay (real-time MSP assay) to define the methylation status of the MGMT promoter. Briefly, genomic DNA is deaminated using sodium bisulphite after isolation. 5-Methyl Cytosine is refractory to this chemical modification. Unmethylated Cytosine quantitatively turns into Uracil during this process. After amplification of the DNA sequences using methylation specific primers, the detection of the amplified DNA sequences is carried out using the amplifluor technology. The modification for the amplifluor primers is 5' FAM internal Dabcyl.

The quantitation process depends on fluorescent light which is emitted only when the detector is bound to its complementary sequence.

Analyte quantitations for several markers additional to MGMT were successfully performed using this technology. These consisted of parallel amplification/quantification processes using specific primer and primer/detector pairs for each analyte using the Amplifluor® assay format on an ABI Prism® 7900HT instrument (Applied Biosystems).

The final primer concentrations in the reaction mix were 100 nM for both forward primer/detector and reverse primer. 12.5 µl of iTaq™ Supermix with Rox (BioRad, 2× buffer) were used per PCR reaction. The total volume per reaction, including 5 µl of modified template DNA, was 25 µl. The ABI 7900HT SDS instrument was started 10 min before use, allowing the heated cover to reach 105° C. The following thermal profile was used: Stage1: 50° C. for 2 min, Stage2: 95° C. for 10 min, Stage3: 95° C. for 15 sec, 62° C. for 1 min (=plateau-data collection) for 45 repeats.

Plasmid material, used as standard curve was generated as follows: the promoter sequence as defined by the primers is PCR amplified and cloned (using suitable isolated and bisulphite modified cell line DNA). The sequence is verified by sequencing and compared to the published promoter sequence.

A standard curve ($2 \times 10^6$-20 copies) was included to determine copy numbers of unknown samples by interpolation of their Ct values to the standard curve. β-Actin was used as a reference gene in the assay.

BRCA1
Primer and Detector Sequences

A BRCA1 amplifluor assay was designed to evaluate the methylation status of the BRCA1 gene in breast cancer patients. Primer and detector sequences are detailed in Table 9.

TABLE 9

Primer and amplifluor detector sequences BRCA1

| Name | Sequence |
|---|---|
| BRCA1 forward detector | 5'-AGCGATGCGTTCGAGCATCGCUTCGTGGTAAC GGAAAAGCGC-3' (SEQ ID NO: 1 plus SEQ ID NO: 6) |
| BRCA1 reverse primer | 5'-AAATCTCAACGAACTCACGCCG-3' (SEQ ID NO: 13) |

Performance Standard Curve

A serial dilution of BRCA1 plasmid material ($2 \times 10^6$ to $2 \times 10^1$ copies/5 µl) was loaded in duplicate using the above specified primer and Amplifluor detector sequences. Results were generated (see Table 10) using the SDS 2.2 software (Applied Biosystems), exported as Ct values (cycle number at which the amplification curves cross the threshold value, set automatically by the software). Good performance of the standard curve was obtained: slope of −3.4147, corresponding to a PCR efficiency of 96% and $R^2$ value of 0.9999.

TABLE 10 performance BRCA1 standard curve

| Quantity Standards | $Ct_1$ | $Ct_2$ | Average Ct | ΔCt |
|---|---|---|---|---|
| 2000000 | 18.39 | 18.33 | 18.36 | 0.06 |
| 200000 | 22.30 | 22.15 | 22.22 | 0.15 |
| 20000 | 26.19 | 26.17 | 26.18 | 0.03 |
| 2000 | 30.12 | 30.24 | 30.18 | 0.11 |
| 200 | 33.97 | 33.92 | 33.95 | 0.04 |
| 20 | 37.92 | 37.90 | 37.91 | 0.02 |
| NTC | 42.30 | 41.55 | 41.93 | |

Clinical Samples

The BRCA1 methylation status was investigated for 40 breast tumor samples and 10 normal breast samples. The Ct values were used to calculate the copy numbers for each sample based on a linear regression of the standard curve values. The BRCA1 copy numbers were divided by the β-Actin copy numbers and multiplied by 1000 for convenient handling; results were referred to as the ratio value (see Table 11). Invalid results are due to β-Actin copy numbers below 200 in the respective samples. The results clearly show that methylated BRCA1 can be distinguished from unmethylated BRCA1 with present assay set up.

TABLE 11

Preliminary results BRCA1 amplifluor assay on clinical material

| Sample | Ct | Copies | Ratio BRCA1/ b-actin (copies) × 1000 | METHYLATION STATUS |
|---|---|---|---|---|
| Tumor 1 | 31.37 | 39.06 | 37.44 | METHYLATED |
| Tumor 2 | 31.21 | 43.55 | 75.26 | METHYLATED |
| Tumor 3 | 31.67 | 31.98 | 59.44 | METHYLATED |

TABLE 11-continued

Preliminary results BRCA1 amplifluor assay on clinical material

| Sample | Ct | Copies | Ratio BRCA1/ b-actin (copies) × 1000 | METHYLATION STATUS |
|---|---|---|---|---|
| Tumor 4 | 30.63 | 64.14 | 87.40 | METHYLATED |
| Tumor 5 | 30.80 | 57.12 | 109.45 | METHYLATED |
| Tumor 6 | 33.99 | 6.74 | 51.38 | INVALID |
| Tumor 7 | 30.45 | 72.42 | 169.91 | METHYLATED |
| Tumor 8 | 30.59 | 65.73 | 113.23 | METHYLATED |
| Tumor 9 | 26.47 | 1047.30 | 1184.29 | METHYLATED |
| Tumor 10 | 27.70 | 458.09 | 184.54 | METHYLATED |
| Tumor 11 | 29.75 | 115.63 | 193.56 | METHYLATED |
| Tumor 12 | 36.27 | 1.45 | 30.51 | INVALID |
| Tumor 13 | 31.47 | 36.53 | 101.88 | METHYLATED |
| Tumor 14 | 32.35 | 20.21 | 55.18 | METHYLATED |
| Tumor 15 | 30.25 | 82.93 | 27.54 | METHYLATED |
| Tumor 16 | 30.47 | 71.36 | 25.67 | METHYLATED |
| Tumor 17 | 30.42 | 73.70 | 37.62 | METHYLATED |
| Tumor 18 | 32.34 | 20.40 | 25.83 | METHYLATED |
| Tumor 19 | 31.40 | 38.22 | 50.15 | METHYLATED |
| Tumor 20 | 31.63 | 32.71 | 54.27 | METHYLATED |
| Tumor 21 | 30.55 | 67.88 | 70.81 | METHYLATED |
| Tumor 22 | 31.67 | 31.99 | 36.60 | METHYLATED |
| Tumor 23 | 31.43 | 37.46 | 108.74 | METHYLATED |
| Tumor 24 | 31.71 | 31.14 | 92.78 | METHYLATED |
| Tumor 25 | 34.85 | 3.77 | 49.66 | INVALID |
| Tumor 26 | 31.50 | 35.70 | 78.28 | METHYLATED |
| Tumor 27 | 31.03 | 49.09 | 135.65 | METHYLATED |
| Tumor 28 | 31.46 | 36.62 | 78.37 | METHYLATED |
| Tumor 29 | 26.66 | 922.65 | 1098.17 | METHYLATED |
| Tumor 30 | 30.72 | 60.18 | 19.55 | METHYLATED |
| Tumor 31 | 30.06 | 94.17 | 62.02 | METHYLATED |
| Tumor 32 | 32.09 | 24.08 | 62.53 | METHYLATED |
| Tumor 33 | 30.11 | 91.01 | 173.98 | METHYLATED |
| Tumor 34 | 34.40 | 5.10 | 116.39 | INVALID |
| Tumor 35 | 39.88 | 0.13 | #DIV/0! | INVALID |
| Tumor 36 | 31.60 | 33.39 | 148.31 | METHYLATED |
| Tumor 37 | 34.17 | 5.95 | 27.68 | UNMETHYLATED |
| Tumor 38 | 38.14 | 0.42 | 47.87 | INVALID |
| Tumor 39 | 39.34 | 0.19 | 176.66 | INVALID |
| Tumor 40 | Undetermined | 0.00 | 0.00 | INVALID |
| Normal 1 | 37.65 | 0.58 | 21.37 | INVALID |
| Normal 2 | 36.84 | 0.99 | 14.18 | INVALID |
| Normal 3 | 38.89 | 0.25 | 7.78 | INVALID |
| Normal 4 | 38.19 | 0.40 | 4.20 | INVALID |
| Normal 5 | 37.66 | 0.57 | 2.11 | UNMETHYLATED |
| Normal 6 | 40.28 | 0.00 | 0.00 | UNMETHYLATED |
| Normal 7 | 35.92 | 1.84 | 23.08 | INVALID |
| Normal 8 | 38.07 | 0.43 | 17.15 | INVALID |
| Normal 9 | 41.77 | 0.00 | 0.00 | INVALID |
| Normal 10 | 41.41 | 0.00 | 0.00 | UNMETHYLATED |
| positive control | 24.12 | 5060.95 | 1143.85 | METHYLATED |
| negative control | 36.79 | 1.03 | 2.58 | UNMETHYLATED |

WRN

Primer and Detector Sequences

Different WRN amplifluor assays were designed to evaluate the methylation status of the WRN gene in colorectal cancer patients. Primer and detector sequences are detailed in Table 12.

TABLE 12

Primer and amplifluor detector sequences WRN

| Name | Sequence |
|---|---|
| WRN_NOR1 forward detector | 5'-AGCGATGCGTTCGAGCATCGCUGTTC GTATTGTTTTTCGTCGGAGTAGTC-3' (SEQ ID NO: 1 plus SEQ ID NO: 14) |
| WRN_NOR1 reverse primer | 5'-CGCAACGACCGCAAAAAAAACG-3' (SEQ ID NO: 15) |
| WRN_NOR1 reverse detector | 5'-AGCGATGCGTTCGAGCATCGCUCGCA ACGACCGCAAAAAAAACG-3' (SEQ ID NO: 1 plus SEQ ID NO: 15) |
| WRN_NOR1 forward primer | 5'-GTTCGTATTGTTTTTCGTCGGAGTAG TC-3' (SEQ ID NO: 14) |
| WRN_NOR2 reverse detector | 5'-AGCGATGCGTTCGAGCATCGCUCCGA CAATAACTAAAACCCCG-3' (SEQ ID NO: 1 plus SEQ ID NO: 16) |
| WRN_NOR2 forward primer | 5'-GGGTGTTGAGAATAATCGTAGAC-3' (SEQ ID NO: 17) |
| WRN_NOR4 forward primer | 5'-GTTTTGTTCGCGTTTTTCGTA-3' (SEQ ID NO: 19) |

Performance Standard Curve

A serial dilution of WRN plasmid material ($2 \times 10^6$ to $2 \times 10^1$ copies/5 µl) was loaded in duplicate using the above specified primer and Amplifluor detector sequences using an optimized thermal profile: Stage1: 50° C. for 2 min, Stage2: 95° C. for 10 min, Stage3: 95° C. for 15 sec, 61° C. for 30 sec, 61° C. for 30 sec (=plateau-data collection) for 45 repeats. Different primer combinations were assessed for WRN. Results were generated (see Table 13) using the SDS 2.2 software (Applied Biosystems), exported as Ct values (cycle number at which the amplification curves cross the threshold value, set automatically by the software). Good performance of the standard curve was obtained for all assays.

TABLE 13 performance WRN standard curve using different primer combinations

| Quantity Standards | Average Ct WRN_NOR1F | Average Ct WRN_NOR1R | Average Ct WRN_NOR2R | Average Ct WRN_NOR4R |
|---|---|---|---|---|
| 2000000 | 14.88 | 15.82 | 14.41 | 16.83 |
| 200000 | 18.70 | 19.90 | 17.84 | 20.62 |
| 20000 | 22.56 | 23.98 | 21.58 | 24.20 |
| 2000 | 26.13 | 28.06 | 25.37 | 27.80 |
| 200 | 30.22 | 32.17 | 29.14 | 31.42 |
| 20 | 33.85 | 35.68 | 33.19 | 34.50 |

TABLE 13-continued performance WRN standard curve using different primer combinations

| Quantity Standards | Average Ct WRN_NOR1F | Average Ct WRN_NOR1R | Average Ct WRN_NOR2R | Average Ct WRN_NOR4R |
|---|---|---|---|---|
| NTC | Undetermined | Undetermined | Undetermined | Undetermined |
| PCR efficiency (%) | 83 | 78 | 84 | 91 |
| $R^2$ | 0.9998 | 0.9996 | 0.9995 | 0.9992 |

(NTC = no-template control)

Clinical Samples

The WRN methylation status was investigated for 56 colorectal cancer samples and 39 normal samples. The Ct values were used to calculate the copy numbers for each sample based on a linear regression of the standard curve values. The WRN copy numbers were divided by the β-Actin copy numbers and multiplied by 1000 for convenient handling; results were referred to as the ratio value (see Table 14). Performance characteristic of the different WRN assays: WRN_NOR1F, WRN_NOR1R, WRN_NOR2R and WRN_NOR4R demonstrated a sensitivity of respectively 41%, 49%, 30% and 50% with a specificity of 100% for the tested CRC.

TABLE 14

Preliminary results WRN amplifluor assay on clinical material

| Samples | Group | ratio WRN_NOR1F/b-actin X1000 | ratio WRN_NOR1R/b-actin X1000 | ratio WRN_NOR2R/b-actin X1000 | ratio WRN_NOR4R/b-actin X1000 |
|---|---|---|---|---|---|
| Cut_off | | 39.07 | 13.44 | 3.23 | 6.70 |
| Specificity % | | 100 | 100 | 100 | 100 |
| Sensitivity % | | 41 | 49 | 30 | 50 |

The different WRN assays were tested on their complementarities for detecting CRC; the best combination was obtained with WRN_NOR1R and WRN_NOR4R. Results are detailed in Table 15.

TABLE 15

Complementary results WRN_NOR1R and WRN_NOR4R

| | Group | Methylated | Unmethylated | Invalid | Valid | Specificity % | Sensitivity % |
|---|---|---|---|---|---|---|---|
| WRN_NOR1R-NOR4R | normal | 0 | 36 | 3 | 36 | 100 | |
| | cancer | 32 | 17 | 7 | 49 | | 65 |

PTEN

Primer and Detector Sequences

Different PTEN amplifluor assays were designed to evaluate the methylation status of the PTEN gene in cancerous patients. Sequence details can be found in Table 16.

TABLE 16

Primer and amplifluor detector sequences PTEN

| Name | Sequence |
|---|---|
| PTEN 11 forward detector | 5'- AGCGATGCGTTCGAGCATCGCUGTGTTTACGTTT AGTACGTTCGGT-3' (SEQ ID NO: 1 plus SEQ ID NO: 20) |
| PTEN 11 reverse primer | 5'-TCATCCGACTCCCTTACAACG-3' (SEQ ID NO: 21) |
| PTEN 12 forward detector | 5'- AGCGATGCGTTCGAGCATCGCUTAGTTTTGGGTG CGAGCGTAG-3' (SEQ ID NO: 1 plus SEQ ID NO: 22) |
| PTEN 12 reverse | 5'-GCGTTACTACAAAAACCGCAA-3' (SEQ ID NO: 23) |
| PTEN 6 forward detector | 5'-AGCGATGCGTTCGAGCATCGCUTGGTATATTTAGG GATTCGGGTC-3' (SEQ ID NO: 1 plus SEQ ID NO: 24) |
| PTEN 6 reverse primer | 5'-AACGAATAATCCTCCGAACG-3' (SEQ ID NO: 25) |

Performance Standard Curve

A serial dilution of PTEN alternative standard curve material ($2 \times 10^6$ to $2 \times 10^1$ copies/5 µl) was loaded in duplicate using the above specified primer and Amplifluor detector sequences. Results were generated using the SDS 2.2 software (Applied Biosystems), exported as Ct values (cycle number at which the amplification curves cross the threshold value, set automatically by the software). Good performance of the standard curve was obtained. Results are summarized in Table 17.

TABLE 17

Summary of slopes and PCR efficiencies PTEN

| Name | Slope | $R^2$ | Efficiency |
|---|---|---|---|
| PTEN 11 standard curve material | 3.6769 | 0.9996 | 87% |
| PTEN 12 standard curve material | 3.5803 | 0.9999 | 90% |
| PTEN 6 standard curve material | 3.3864 | 0.9974 | 97% |

NDRG4
Primer and Detector Sequences

Different NDRG4 amplifluor assays were tested to evaluate the methylation status of the NDRG4 gene in colorectal cancer patients. Especially short amplifluor assays were designed to favour the detection of low-molecular-weight DNA, often present in plasma/serum samples in the form of fragmented DNA. Primer and detector sequences are detailed in Table 18.

TABLE 18

Primer and amplifluor sequences NDRG4

| Name | 5' to 3' Sequences Detector Modifications: 5' FAM and internal dUdabcyl |
|---|---|
| NDRGR_66304_S_AMP forward detector | AGCGATGCGTTCGAGCATCGCUTTCGGTGA ATTTTAGGAGGC (SEQ ID NO: 1 plus SEQ ID NO: 26) |
| NDRG4_66304_AS reverse primer | TCGAACGACGAACACGAAA (SEQ ID NO: 27) |
| NDRG4_72006_S_AMP forward detector | AGCGATGCGTTCGAGCATCGCUCGTTCGGG ATTAGTTTTAGGTTC (SEQ ID NO: 1 plus SEQ ID NO: 28) |
| NDRG4_72006_AS reverse primer | AATTTAACGAATATAAACGCTCG (SEQ ID NO: 29) |
| NDRG4_72007_S_AMP forward detector | AGCGATGCGTTCGAGCATCGCUGGTATTTT AGTCGCGTAGAAGGC (SEQ ID NO: 1 plus SEQ ID NO: 30) |
| NDRG4_72007_AS reverse primer | ACTAATCCCGAACGAACCG (SEQ ID NO: 31) |
| NDRG4_72008_S forward primer | CGTTCGGAGTTCGTTTTAATTC (SEQ ID NO: 32) |
| NDRG4_72008_AS_AMP Reverse detector | AGCGATGCGTTCGAGCATCGCUCTACTCAC AAATACCGCCCG (SEQ ID NO: 1 plus SEQ ID NO: 33) |

Performance Standard Curve

A serial dilution of NDRG4 alternative standard curve material ($9.6 \times 10^5$ to $9.6 \times 10^1$ copies/5 µl) was loaded in duplicate using the above specified primer and Amplifluor detector sequences.

Alternative standard curve material was generated as follow: the promoter sequence as defined by the primers was PCR amplified, loaded on gel to check its specificity, subsequently purified and quantified using the Picogreen® dsDNA quantitation kit (Molecular Probes, #P7589) according to the manufacturer's recommendations.

2.4 µl of standard curve dilution was added to a final 12 µl PCR reaction mix volume containing: 6 µl of QuantiTect Multiplex Master Mix (Qiagen, 2× buffer) and final primer concentrations of 100 nM for both primer and detector sequences.

Cycling conditions for each NDRG4 design were 95° C. for 15 min; followed by 45 cycles of 94° C. for 15 sec, 57° C. for 30 sec [62° C. for NDRG4_72008] and 57° C. for 30 sec [62° C. for NDRG4_72008] (=plateau-data collection).

Different primer combinations were assessed for NDRG4. Results were generated (see Table 19) using the SDS 2.2.2 software from Applied Biosystems with automatic baseline and threshold settings. Good performance of the standard curve was obtained for all assays.

TABLE 19 performance NDRG4 standard curve using different primer combinations

| Assay name | Amplicon length | Slope | $R^2$ | Efficiency | NTC |
|---|---|---|---|---|---|
| NDRG4_66304 | 107 | 3.3800 | 0.9994 | 97.6% | negative |
| NDRG4_72006 | 85 | 3.6402 | 0.9987 | 88.2% | negative |
| NDRG4_72007 | 86 | 3.4834 | 0.9998 | 93.7% | negative |
| NDRG4_72008 | 92 | 3.2681 | 0.9999 | 102.3% | negative |

Clinical Samples
1) Evaluation Sensitivity of NDRG4 Amplifuor Assays Using Diluted Plasma Samples from Patients Diagnosed with CRC 10 plasma samples from colorectal cancer patients (stage IV and III) were provided by Signature Diagnostics. Each sample was split in 3 and diluted with plasma from healthy volunteers (control) according to following dilution scheme:
Condition A: 2 ml CRC plasma+2 ml control plasma
Condition B: 1 ml CRC plasma+3 ml control plasma
Condition C: 2 ml control plasma (negative control)

Genomic DNA was extracted using a standard method (phenol/chloroform), followed by sodium bisulfite treatment (BT) using the EZ DNA Methylation kit from Zymo Research. The chemically treated DNA was used as template for real-time MSP. Methylation levels of the NDRG4 gene promoter were determined by real-time MSP using specific primers and probes for the molecular beacon format NDRG4_1a (details of this assay have previously been provided in International Publication WO08/084219) and amplifluor format: NDRG4_72007 and NDRG4_72008.

Recovered copy numbers were calculated based on a linear regression of the standard curve and compared for each different condition.

TABLE 20 copy number recovery NDRG4 beacon format versus amplifluor format

| Condition samples | copies NDRG4_1a (beacon) | Copies NDRG4_72007 (amplifluor) | Copies NDRG4_72008 (amplifluor) |
|---|---|---|---|
| Sample 1-A | 2.12 | 31.55 | 23.43 |
| Sample 2-A | 0.00 | 0.00 | 0.92 |
| Sample 3-A | 0.00 | 0.00 | 0.00 |
| Sample 4-A | 33.18 | 265.55 | 107.16 |
| Sample 5-A | 0.00 | 3.31 | 0.00 |
| Sample 6-A | 19.55 | 369.07 | 675.73 |
| Sample 7-A | 2.64 | 12.00 | 23.23 |
| Sample 8-A | 0.00 | 0.00 | 54.09 |

TABLE 20-continued copy number recovery NDRG4 beacon format versus amplifluor format

| Condition samples | copies NDRG4_1a (beacon) | Copies NDRG4_72007 (amplifluor) | Copies NDRG4_72008 (amplifluor) |
|---|---|---|---|
| Sample 9-A | 0.00 | 0.00 | 0.00 |
| Sample 10-A | 0.00 | 0.00 | 2.03 |
| Sample 1-B | 2.97 | 13.84 | 39.15 |
| Sample 2-B | 0.00 | 0.00 | 0.89 |
| Sample 3-B | 0.00 | 0.00 | 0.00 |
| Sample 4-B | 42.13 | 321.51 | 76.25 |
| Sample 5-B | 0.00 | 0.00 | 1.40 |
| Sample 6-B | N/A | N/A | N/A |
| Sample 7-B | 0.00 | 5.53 | 0.00 |
| Sample 8-B | N/A | N/A | N/A |
| Sample 9-B | 0.00 | 0.00 | 2.16 |
| Sample 10-B | 0.00 | 0.00 | 0.00 |
| Sample 1-C | 0.00 | 0.00 | 10.05 |
| Sample 2-C | 3.68 | 0.00 | 0.00 |

TABLE 20-continued copy number recovery NDRG4 beacon format versus amplifluor format

| Condition samples | copies NDRG4_1a (beacon) | Copies NDRG4_72007 (amplifluor) | Copies NDRG4_72008 (amplifluor) |
|---|---|---|---|
| Sample 3-C | 0.00 | 0.00 | 0.00 |
| Sample 4-C | 0.00 | 0.00 | 1.00 |
| Sample 5-C | 0.00 | 0.00 | 0.00 |
| Sample 6-C | 0.00 | 0.00 | 0.00 |
| Sample 7-C | 0.00 | 0.00 | 4.58 |
| Sample 8-C | 0.00 | 0.00 | 0.00 |
| Sample 9-C | 0.00 | 0.00 | 5.64 |
| Sample 10-C | 0.00 | 0.00 | 0.98 |
| pos control | 5671.29 | 23164.81 | 18937.12 |
| neg control | 0.00 | 0.00 | 0.00 |

Results are presented in Table 20. Higher copy numbers are obtained using the amplifluor format. Performance characteristics of the different NDRG4 assays: NDRG4_1a (beacon), NDRG4_72007 (amplifluor), and NDRG4_72008 (amplifluor) demonstrated a sensitivity of respectively 20%, 50%, and 50% with a specificity of 100% for the tested CRC diluted plasma samples. These preliminary data indicate that a short amplifluor assay could provide a better alternative than beacon assay (technically difficult to shorten the assay) for CRC methylation detection in plasma DNA samples (high DNA fragmentation nature).

2) NDRG4_72007 Amplifluor Assay and NDRG4_1a Beacon Assay Tested on Tissue Samples The NDRG4 methylation status was further investigated in 88 CRC FFPE (formalin fixed paraffin embedded) samples and 10 normal FFPE samples.

Formalin Fixed paraffin embedded samples were first de-paraffinized in 750 µl xylene for 2 h. Then, 250 µl of 70% ethanol was added before centrifugation at 13000 rpm for 15 min. The supernatant was removed and the samples were air dried at room temperature.

Genomic DNA was extracted using a standard method (phenol/chloroform), followed by sodium bisulfite treatment (BT) using the EZ DNA Methylation kit from Zymo Research. 1.5 µl of chemically treated DNA was used as template for real-time MSP. Methylation levels of the NDRG4 gene promoter were determined by real-time MSP using specific primers and probes for the molecular beacon format NDRG4_1a and amplifluor format: NDRG4_72007. Several annealing temperatures were investigated (57° C., 62° C. and 80.5° C.) to further optimize the NDRG4_72007 amplifluor assay.

The results presented in Table 21 clearly indicate that present NDRG4 assay set-ups, discriminate between cancers and non-cancers.

TABLE 21

Performance characteristics for NDRG4_1a and NDRG4_72007

| | NDRG4_1a (beacon) | NDRG4_72007 57° C. (amplifluor) | NDRG4_72007 62° C. (amplifluor) | NDRG4_72007 80.5° C. (amplifluor) |
|---|---|---|---|---|
| | No cut-off applied | | | |
| Sensitivity (%) | 57 | 83 | 71 | 56 |
| Specificity (%) | 93 | 64 | 95 | 100 |
| | Cut-off applied to obtain 100% specificity | | | |
| Cut-off ratio | 2.26 | 80 | 390 | / |
| Sensitivity (%) | 55 | 78 | 63 | / |

EXAMPLE 4

Reproducibility of the MGMT Amplifluor Assay

To test the reproducibility of the MGMT amplifluor assay as described in example 1, 75 available clinical samples were processed twice through real-time MSP: once at OncoMethylome Sciences (ONCO) and once at Laboratory Corporation of America@ Holdings (LabCorp®). Both laboratories obtained comparable results.

Materials and Methods

Sample Preparation 75 formalin-fixed, paraffin-embedded (FFPE) glioma tissue samples were available for testing through the MGMT amplifluor real-time MSP. For each glioma tumor sample, 4 10 µm consecutive sections were prepared on glass slides. The prepared sample sections were then divided between the 2 sites and processed in parallel (including sample preparation) according to each laboratory's respective protocols (both real-time MSP). LabCorp® was blinded to the results obtained by ONCO.

Real-Time MSP Protocol Followed by ONCO

DNA isolation, modification and analyte quantitations were conducted as previously described in example 1; amplification conditions were subject to the following modifications:

iTaq™ Supermix with Rox (BioRad, 2× buffer) was replaced by Quantitect buffer (Qiagen, 2× buffer)

Stage3 of the thermal profile was further optimized: 95° C. for 15 sec, 62° C. for 30 sec and 62° C. for 30 sec (=plateau-data collection)

Technical test run validation criteria used to classify samples as methylated, non-methylated or invalid are described in Table 22. A cutoff of 8 was used for classification of non-methylated and methylated MGMT.

TABLE 22

MGMT validation criteria

| Results | copy# (mMGMT) | copy# (β-actin) | Ratio × 1000 |
|---|---|---|---|
| Methylated MGMT | ≥10 | ≥10 | ≥8 |
| Non-Methylated | ≥10 | ≥10 | <8 |
| MGMT | <10 | ≥1250 | / |
| Invalid | <10 | <1250 | / |
|  | any | <10 | / |

Real-Time MSP Protocol Followed by LabCorp®

Genomic DNA extraction, purification and modification was according to the in-house procedure used at LabCorp® Real-time MSP procedure was conducted similarly to the protocol followed by ONCO.

Technical test run validation criteria are described in Table 22.

Results

Several patient samples were processed in parallel in independent laboratories to confirm the reproducibility of the MGMT assay. Sample processing was performed according to each laboratory's respective protocol. In total, 75 glioma (glioblastoma) samples, blinded to LabCorp®, were processed through the MGMT assay as specified in materials and methods to demonstrate similar results obtained at ONCO. Results obtained in each laboratory are indicated in Table 23.

TABLE 23

Results 75 glioma samples ONCO versus LabCorp ®

| Sample # | ONCO | LabCorp ® |
|---|---|---|
| 1 | Non-methylated | Non-methylated |
| 2 | Non-methylated | Non-methylated |
| 3 | Methylated | Methylated |
| 4 | Non-methylated | Non-methylated |
| 5 | Non-methylated | Non-methylated |
| 6 | Methylated | Methylated |
| 7 | Non-methylated | Non-methylated |
| 8 | Methylated | Methylated |
| 9 | Methylated | Methylated |
| 10 | Non-methylated | Non-methylated |
| 11 | Methylated | Methylated |
| 12 | Non-methylated | Non-methylated |
| 13 | Non-methylated | Non-methylated |
| 14 | Non-methylated | Non-methylated |
| 15 | Non-methylated | Non-methylated |
| 16 | Non-methylated | Non-methylated |
| 17 | Non-methylated | Non-methylated |
| 18 | Methylated | Methylated |
| 19 | Methylated | Methylated |
| 20 | Non-methylated | Non-methylated |
| 21 | Non-methylated | Non-methylated |
| 22 | Methylated | Methylated |
| 23 | Non-methylated | Non-methylated |
| 24 | Methylated | Methylated |
| 25 | Non-methylated | Non-methylated |
| 26 | Non-methylated | Non-methylated |
| 27 | Methylated | Methylated |
| 28 | Non-methylated | Non-methylated |
| 29 | Non-methylated | Non-methylated |
| 30 | Non-methylated | Non-methylated |
| 31 | Methylated | Methylated |
| 32 | Methylated | Methylated |
| 33 | Non-methylated | Invalid |
| 34 | Non-methylated | Non-methylated |
| 35 | Methylated | Methylated |
| 36 | Non-methylated | Non-methylated |
| 37 | Non-methylated | Non-methylated |
| 38 | Non-methylated | Non-methylated |
| 39 | Non-methylated | Non-methylated |
| 40 | Non-methylated | Invalid |
| 41 | Non-methylated | Invalid |
| 42 | Non-methylated | Invalid |
| 43 | Non-methylated | Invalid |
| 44 | Non-methylated | Invalid |
| 45 | Non-methylated | Non-methylated |
| 46 | Non-methylated | Non-methylated |
| 47 | Non-methylated | Invalid |
| 48 | Non-methylated | Invalid |
| 49 | Non-methylated | Invalid |
| 50 | Non-methylated | Non-methylated |
| 51 | Non-methylated | Invalid |
| 52 | Non-methylated | Non-methylated |
| 53 | Methylated | Methylated |
| 54 | Non-methylated | Non-methylated |
| 55 | Non-methylated | Non-methylated |
| 56 | Non-methylated | Non-methylated |
| 57 | Non-methylated | Non-methylated |
| 58 | Methylated | Methylated |
| 59 | Methylated | Invalid |
| 60 | Methylated | Methylated |
| 61 | Non-methylated | Non-methylated |
| 62 | Methylated | Methylated |
| 63 | Non-methylated | Non-methylated |
| 64 | Non-methylated | Invalid |
| 65 | Non-methylated | Non-methylated |
| 66 | Methylated | Methylated |
| 67 | Non-methylated | Non-methylated |
| 68 | Methylated | Methylated |
| 69 | Invalid | Invalid |
| 70 | Non-methylated | Non-methylated |
| 71 | Methylated | Methylated |
| 72 | Non-methylated | Non-methylated |
| 73 | Methylated | Methylated |
| 74 | Methylated | Methylated |
| 75 | Methylated | Methylated |

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all embodiments described herein are considered to be broadly applicable and combinable with any and all other consistent embodiments, as appropriate.

Various publications are cited herein, the disclosures of which are incorporated by reference in their entireties.

The invention claimed is:

1. A real-time method of detecting the presence and/or amount of a methylated or unmethylated gene of interest in a DNA-containing sample, comprising:
   (a) contacting the DNA-containing sample with a reagent which selectively modifies unmethylated cytosine residues in the DNA to produce detectable modified residues but which does not modify methylated cytosine residues
   (b) amplifying at least a portion of the methylated or unmethylated gene of interest using at least one primer pair, at least one primer of which is designed to bind only to the sequence of methylated or unmethylated DNA following treatment with the reagent, wherein at least one primer in the primer pair is a primer containing a stem loop structure carrying a donor and an acceptor moiety of a molecular energy transfer pair arranged such that in the absence of amplification, the acceptor moiety quenches fluorescence emitted by the donor moiety upon excitation and during amplification, the stem loop structure is disrupted so as to separate the donor and acceptor moieties sufficiently to produce a detectable fluorescence signal which is detected in real-time to provide an indication of the gene copy number of the methylated or unmethylated gene of interest
   (c) quantifying the results of the real-time detection against a standard curve for the methylated or unmethylated gene of interest to produce an output of gene copy number; characterised in that the amplification is considered valid where the cycle threshold value is less than 40,
   further characterised in that the amplification is considered valid where in a parallel reaction using the same reagents, there is no amplification of a sample containing no DNA at the cycle threshold value of less than 40 and further characterised in that the amplifying is carried out using the polymerase chain reaction and the data collection step is carried out at between 60° C. and 64° C., and
   wherein the methylated gene of interested is MGMT and the at least one primer pair for amplifying at least a portion of the methylated MGMT gene comprises primers comprising the sequences set forth as SEQ ID NO: 2 and SEQ ID NO: 3.

2. The method of claim 1 further characterised in amplifying at least a portion of a reference gene using at least one primer pair, wherein at least one primer in the primer pair is a primer containing a stem loop structure carrying a donor and an acceptor moiety of a molecular energy transfer pair arranged such that in the absence of amplification, the acceptor moiety quenches fluorescence emitted by the donor moiety upon excitation and during amplification, the stem loop structure is disrupted so as to separate the donor and acceptor moieties sufficiently to produce a detectable fluorescence signal which is detected in real-time to provide an indication of the gene copy number of the reference gene.

3. The method of claim 2 further characterised in that the results of the real-time detection are quantified against both a standard curve for the methylated or unmethylated gene of interest and reference gene respectively to produce an output of gene copy number and the results are normalised by dividing the gene copy number of the methylated or unmethylated gene of interest by the gene copy number of the reference gene.

4. The method of claim 1 further characterised in that the amplification is considered valid where:
   (a) the slope of the standard curve for the methylated or unmethylated gene of interest and optionally the reference gene is at least −4, indicating an amplification efficiency of at least 77%,
   (b) the coefficient of determination (R2) for at least four data points on the standard curve or curves is above 0.99;
   (c) in a parallel reaction using the same reagents, there is detectable amplification of a positive control sample known to contain the gene of interest in methylated or unmethylated form at the cycle threshold value of less than 40; or
   (d) in a parallel reaction using the same reagents, there is no detectable amplification of a negative control sample known to contain the gene of interest in unmethylated or methylated form at the cycle threshold value of less than 40.

5. The method of claim 4, wherein the positive control sample known to contain methylated MGMT is derived from SW48 cells and/or the negative control sample known to contain unmethylated MGMT is derived from HT29 cells.

6. The method of claim 1, wherein the at least one primer pair for amplification of the methylated or unmethylated gene of interest/reference gene is used in the amplification at a concentration of approximately 50 to 150 nM or at a concentration of approximately 100 nM.

7. The method of claim 1, wherein the data-collection step is carried out at 62° C.

8. The method of claim 7, wherein the thermal profiling of the polymerase chain reaction comprises approximately 45 repeats of the cycle:
   (a) 50° C. for 2 minutes
   (b) 95° C. for 10 minutes
   (c) 95° C. for 15 seconds
   (d) 62° C. for 1 minute.

9. The method of claim 1, wherein the at least one primer pair for amplification of the methylated or unmethylated gene of interest/reference gene produces an amplification product of between approximately 50 and 250 bp or produces an amplification product of between approximately 100 and 200 bp.

10. The method of claim 2, wherein amplification of the gene of interest and reference gene is carried out simultaneously in the same reaction.

11. The method of claim 1, wherein the total reaction volume for the amplification step is around 25 μl.

12. A real-time method of detecting the presence and/or amount of a methylated or unmethylated gene of interest in a DNA-containing sample, comprising:

(a) contacting the DNA-containing sample with a reagent which selectively modifies unmethylated cytosine residues in the DNA to produce detectable modified residues but which does not modify methylated cytosine residues (b) amplifying at least a portion of the methylated or unmethylated gene of interest using at least one primer pair, at least one primer of which is designed to bind only to the sequence of methylated or unmethylated DNA following treatment with the reagent, wherein at least one primer in the primer pair is a primer containing a stem loop structure carrying a donor and an acceptor moiety of a molecular energy transfer pair arranged such that in the absence of amplification, the acceptor moiety quenches fluorescence emitted by the donor moiety upon excitation and during amplification, the stem loop structure is disrupted so as to separate the donor and acceptor moieties sufficiently to produce a detectable fluorescence signal which is detected in real-time to provide an indication of the gene copy number of the methylated or unmethylated gene of interest (c) quantifying the results of the real-time detection against a standard curve for the methylated or unmethylated gene of interest to produce an output of gene copy number; characterised in that the amplification is considered valid where the cycle threshold value is less than 40, and wherein the methylated gene of interested is MGMT and the at least one primer pair for amplifying at least a portion of the methylated MGMT gene comprises primers comprising the sequences set forth as SEQ ID NO: 2 and SEQ ID NO: 3.

13. The method of claim 12 further characterised in amplifying at least a portion of a reference gene using at least one primer pair, wherein at least one primer in the primer pair is a primer containing a stem loop structure carrying a donor and an acceptor moiety of a molecular energy transfer pair arranged such that in the absence of amplification, the acceptor moiety quenches fluorescence emitted by the donor moiety upon excitation and during amplification, the stem loop structure is disrupted so as to separate the donor and acceptor moieties sufficiently to produce a detectable fluorescence signal which is detected in real-time to provide an indication of the gene copy number of the reference gene.

14. The method of claim 13 further characterised in that the results of the real-time detection are quantified against both a standard curve for the methylated or unmethylated gene of interest and reference gene respectively to produce an output of gene copy number and the results are normalised by dividing the gene copy number of the methylated or unmethylated gene of interest by the gene copy number of the reference gene.

15. The method of claim 12 further characterised in that the amplification is considered valid where:
    (a) the slope of the standard curve for the methylated or unmethylated gene of interest and optionally the reference gene is at least −4, indicating an amplification efficiency of at least 77%,
    (b) the coefficient of determination (R2) for at least four data points on the standard curve or curves is above 0.99;
    (c) in a parallel reaction using the same reagents, there is detectable amplification of a positive control sample known to contain the gene of interest in methylated or unmethylated form at the cycle threshold value of less than 40; or
    (d) in a parallel reaction using the same reagents, there is no detectable amplification of a negative control sample known to contain the gene of interest in unmethylated or methylated form at the cycle threshold value of less than 40.

16. The method of claim 15, wherein the positive control sample known to contain methylated MGMT is derived from SW48 cells and/or the negative control sample known to contain unmethylated MGMT is derived from HT29 cells.

17. The method of claim 12, wherein the at least one primer pair for amplification of the methylated or unmethylated gene of interest/reference gene is used in the amplification at a concentration of approximately 50 to 150 nM or at a concentration of approximately 100 nM.

18. The method of claim 12, wherein the data-collection step is carried out at 62° C.

19. The method of claim 18, wherein the thermal profiling of the polymerase chain reaction comprises approximately 45 repeats of the cycle:
    (a) 50° C. for 2 minutes
    (b) 95° C. for 10 minutes
    (c) 95° C. for 15 seconds
    (d) 62° C. for 1 minute.

20. The method of claim 12, wherein the at least one primer pair for amplification of the methylated or unmethylated gene of interest/reference gene produces an amplification product of between approximately 50 and 250 bp or produces an amplification product of between approximately 100 and 200 bp.

21. The method of claim 13, wherein amplification of the gene of interest and reference gene is carried out simultaneously in the same reaction.

22. The method of claim 12, wherein the total reaction volume for the amplification step is around 25 µl.

* * * * *

SEQUENCE LISTING

<160> NUMBER OF SEQ ID NOS: 33

<210> SEQ ID NO 1
<211> LENGTH: 22

```
<212> TYPE: DNA
<213> ORGANISM: Artificial
<220> FEATURE:
<223> OTHER INFORMATION: Primer
<220> FEATURE:
<221> NAME/KEY: u
<222> LOCATION: (22)..(22)
<223> OTHER INFORMATION: u = uracil

<400> SEQUENCE: 1
agcgatgcgt tcgagcatcg cu                                              22

<210> SEQ ID NO 2
<211> LENGTH: 23
<212> TYPE: DNA
<213> ORGANISM: Artificial
<220> FEATURE:
<223> OTHER INFORMATION: Primer

<400> SEQUENCE: 2
tttcgacgtt cgtaggtttt cgc                                             23

<210> SEQ ID NO 3
<211> LENGTH: 22
<212> TYPE: DNA
<213> ORGANISM: Artificial
<220> FEATURE:
<223> OTHER INFORMATION: Primer

<400> SEQUENCE: 3
ctcgaaacta ccaccgtccc ga                                              22

<210> SEQ ID NO 4
<211> LENGTH: 26
<212> TYPE: DNA
<213> ORGANISM: Artificial
<220> FEATURE:
<223> OTHER INFORMATION: Primer

<400> SEQUENCE: 4
tagggagtat ataggttggg gaagtt                                          26

<210> SEQ ID NO 5
<211> LENGTH: 27
<212> TYPE: DNA
<213> ORGANISM: Artificial
<220> FEATURE:
<223> OTHER INFORMATION: Primer

<400> SEQUENCE: 5
aacacacaat aacaaacaca aattcac                                         27

<210> SEQ ID NO 6
<211> LENGTH: 20
<212> TYPE: DNA
<213> ORGANISM: Artificial
<220> FEATURE:
<223> OTHER INFORMATION: Primer

<400> SEQUENCE: 6
tcgtggtaac ggaaaagcgc                                                 20

<210> SEQ ID NO 7
<211> LENGTH: 22
<212> TYPE: DNA
<213> ORGANISM: Artificial
<220> FEATURE:
```

<223> OTHER INFORMATION: Primer

<400> SEQUENCE: 7
gcactcttcc gaaaacgaaa cg                                    22

<210> SEQ ID NO 8
<211> LENGTH: 24
<212> TYPE: DNA
<213> ORGANISM: Artificial
<220> FEATURE:
<223> OTHER INFORMATION: Primer

<400> SEQUENCE: 8
taaaaacgcc tacaaaacca ctcg                                  24

<210> SEQ ID NO 9
<211> LENGTH: 24
<212> TYPE: DNA
<213> ORGANISM: Artificial
<220> FEATURE:
<223> OTHER INFORMATION: Primer

<400> SEQUENCE: 9
aaaaacgcct acaaaaccac tcga                                  24

<210> SEQ ID NO 10
<211> LENGTH: 21
<212> TYPE: DNA
<213> ORGANISM: Artificial
<220> FEATURE:
<223> OTHER INFORMATION: Primer

<400> SEQUENCE: 10
ctcgaaacta ccaccgtccc g                                     21

<210> SEQ ID NO 11
<211> LENGTH: 23
<212> TYPE: DNA
<213> ORGANISM: Artificial
<220> FEATURE:
<223> OTHER INFORMATION: Primer

<400> SEQUENCE: 11
actccgcact cttccgaaaa cga                                   23

<210> SEQ ID NO 12
<211> LENGTH: 23
<212> TYPE: DNA
<213> ORGANISM: Artificial
<220> FEATURE:
<223> OTHER INFORMATION: Primer

<400> SEQUENCE: 12
aactccgcac tcttccgaaa acg                                   23

<210> SEQ ID NO 13
<211> LENGTH: 22
<212> TYPE: DNA
<213> ORGANISM: Artificial
<220> FEATURE:
<223> OTHER INFORMATION: Primer

<400> SEQUENCE: 13
aaatctcaac gaactcacgc cg                                    22

```
<210> SEQ ID NO 14
<211> LENGTH: 28
<212> TYPE: DNA
<213> ORGANISM: Artificial
<220> FEATURE:
<223> OTHER INFORMATION: Primer

<400> SEQUENCE: 14
gttcgtattg tttttcgtcg gagtagtc                                          28

<210> SEQ ID NO 15
<211> LENGTH: 22
<212> TYPE: DNA
<213> ORGANISM: Artificial
<220> FEATURE:
<223> OTHER INFORMATION: Primer

<400> SEQUENCE: 15
cgcaacgacc gcaaaaaaaa cg                                                22

<210> SEQ ID NO 16
<211> LENGTH: 21
<212> TYPE: DNA
<213> ORGANISM: Artificial
<220> FEATURE:
<223> OTHER INFORMATION: Primer

<400> SEQUENCE: 16
ccgacaataa ctaaaacccc g                                                 21

<210> SEQ ID NO 17
<211> LENGTH: 23
<212> TYPE: DNA
<213> ORGANISM: Artificial
<220> FEATURE:
<223> OTHER INFORMATION: Primer

<400> SEQUENCE: 17
gggtgttgag aataatcgta gac                                               23

<210> SEQ ID NO 18
<211> LENGTH: 21
<212> TYPE: DNA
<213> ORGANISM: Artificial
<220> FEATURE:
<223> OTHER INFORMATION: Primer

<400> SEQUENCE: 18
taatataaat acccgccgac t                                                 21

<210> SEQ ID NO 19
<211> LENGTH: 21
<212> TYPE: DNA
<213> ORGANISM: Artificial
<220> FEATURE:
<223> OTHER INFORMATION: Primer

<400> SEQUENCE: 19
gttttgttcg cgttttttcgt a                                                21

<210> SEQ ID NO 20
<211> LENGTH: 24
<212> TYPE: DNA
<213> ORGANISM: Artificial
<220> FEATURE:
<223> OTHER INFORMATION: Primer
```

<400> SEQUENCE: 20
gtgtttacgt ttagtacgtt cggt                                              24

<210> SEQ ID NO 21
<211> LENGTH: 21
<212> TYPE: DNA
<213> ORGANISM: Artificial
<220> FEATURE:
<223> OTHER INFORMATION: Primer

<400> SEQUENCE: 21
tcatccgact cccttacaac g                                                 21

<210> SEQ ID NO 22
<211> LENGTH: 21
<212> TYPE: DNA
<213> ORGANISM: Artificial
<220> FEATURE:
<223> OTHER INFORMATION: Primer

<400> SEQUENCE: 22
tagttttggg tgcgagcgta g                                                 21

<210> SEQ ID NO 23
<211> LENGTH: 21
<212> TYPE: DNA
<213> ORGANISM: Artificial
<220> FEATURE:
<223> OTHER INFORMATION: Primer

<400> SEQUENCE: 23
gcgttactac aaaaaccgca a                                                 21

<210> SEQ ID NO 24
<211> LENGTH: 23
<212> TYPE: DNA
<213> ORGANISM: Artificial
<220> FEATURE:
<223> OTHER INFORMATION: Primer

<400> SEQUENCE: 24
tggtatattt agggattcgg gtc                                               23

<210> SEQ ID NO 25
<211> LENGTH: 20
<212> TYPE: DNA
<213> ORGANISM: Artificial
<220> FEATURE:
<223> OTHER INFORMATION: Primer

<400> SEQUENCE: 25
aacgaataat cctccgaacg                                                   20

<210> SEQ ID NO 26
<211> LENGTH: 20
<212> TYPE: DNA
<213> ORGANISM: Artificial
<220> FEATURE:
<223> OTHER INFORMATION: Primer

<400> SEQUENCE: 26
ttcggtgaat tttaggaggc                                                   20

<210> SEQ ID NO 27
<211> LENGTH: 19

```
<212> TYPE: DNA
<213> ORGANISM: Artificial
<220> FEATURE:
<223> OTHER INFORMATION: Primer

<400> SEQUENCE: 27
tcgaacgacg aacacgaaa                                                  19

<210> SEQ ID NO 28
<211> LENGTH: 23
<212> TYPE: DNA
<213> ORGANISM: Artificial
<220> FEATURE:
<223> OTHER INFORMATION: Primer

<400> SEQUENCE: 28
cgttcgggat tagttttagg ttc                                             23

<210> SEQ ID NO 29
<211> LENGTH: 23
<212> TYPE: DNA
<213> ORGANISM: Artificial
<220> FEATURE:
<223> OTHER INFORMATION: Primer

<400> SEQUENCE: 29
aatttaacga atataaacgc tcg                                             23

<210> SEQ ID NO 30
<211> LENGTH: 23
<212> TYPE: DNA
<213> ORGANISM: Artificial
<220> FEATURE:
<223> OTHER INFORMATION: Primer

<400> SEQUENCE: 30
ggtattttag tcgcgtagaa ggc                                             23

<210> SEQ ID NO 31
<211> LENGTH: 19
<212> TYPE: DNA
<213> ORGANISM: Artificial
<220> FEATURE:
<223> OTHER INFORMATION: Primer

<400> SEQUENCE: 31
actaatcccg aacgaaccg                                                  19

<210> SEQ ID NO 32
<211> LENGTH: 22
<212> TYPE: DNA
<213> ORGANISM: Artificial
<220> FEATURE:
<223> OTHER INFORMATION: Primer

<400> SEQUENCE: 32
cgttcggagt tcgttttaat tc                                              22

<210> SEQ ID NO 33
<211> LENGTH: 20
<212> TYPE: DNA
<213> ORGANISM: Artificial
```

```
<220> FEATURE:
<223> OTHER INFORMATION: Primer

<400> SEQUENCE: 33
ctactcacaa ataccgcccg                                                    20
```